United States Patent [19]

Mertens et al.

[11] Patent Number: 4,851,406

[45] Date of Patent: Jul. 25, 1989

[54] HETEROCYCLIC-SUBSTITUTED INDOLES AND PHARMACEUTICAL COMPOSITIONS CONTAINING THEM

[75] Inventors: Alfred Mertens, Schriesheim; Wolfgang von der Saal, Weinheim; Walter-Gunar Friebe, Mannheim; Bernd Müller-Beckmann, Grunstadt; Gisbert Sponer, Laudenbach, all of Fed. Rep. of Germany

[73] Assignee: Boehringer Mannheim GmbH, Mannheim, Fed. Rep. of Germany

[21] Appl. No.: 904,092

[22] Filed: Sep. 4, 1986

[30] Foreign Application Priority Data

Sep. 5, 1985 [DE] Fed. Rep. of Germany ....... 3531658

[51] Int. Cl.$^4$ .................... A61K 31/40; A61K 31/50; A61K 31/54; A61K 31/535
[52] U.S. Cl. .................. 514/212; 514/242; 514/245; 514/253; 514/269; 514/272; 514/274; 514/275; 514/318; 514/323; 514/333; 514/339; 514/361; 514/362; 514/363; 514/364; 514/365; 514/369; 514/370; 514/372; 514/374; 514/376; 514/377; 514/378; 514/380; 514/381; 514/383; 514/384; 514/385; 514/386; 514/389; 514/390; 514/391; 514/392; 514/397; 514/403; 514/404; 514/406; 514/407; 514/414; 514/415; 514/419; 514/254; 514/228.2; 514/229.2; 514/235.2; 540/596; 540/598; 540/601; 540/602; 540/603; 544/3; 544/8; 544/58.2; 544/54; 544/55; 544/56; 544/63; 544/68; 544/88; 544/98; 544/120; 544/123; 544/131; 544/132; 544/139; 544/143; 544/179; 544/182; 544/238; 544/295; 544/296; 544/300; 544/310; 544/315; 544/316; 544/317; 544/319; 544/320; 544/324; 544/328; 544/331; 544/333; 544/357; 544/405; 546/193; 546/194; 546/201; 546/256; 546/273; 548/127; 548/128; 548/129; 548/130; 548/125; 548/131; 548/132; 548/133; 548/134; 548/135; 548/136; 548/142; 548/143; 548/144; 548/181; 548/213; 548/214; 548/225; 548/226; 548/227; 548/228; 548/229; 548/230; 548/231; 548/233; 548/235; 548/236; 548/251; 548/252; 548/253; 548/254; 548/255; 548/263; 548/264; 548/265; 548/266; 548/267; 548/269; 548/301; 548/307; 548/309; 548/311; 548/312; 548/313; 548/336; 548/361; 548/362; 548/364; 548/374; 548/466; 548/467; 548/468

[58] Field of Search ............... 514/212, 222, 226, 227, 514/228, 229, 230, 232, 233, 234, 236–239, 242, 245, 253, 269, 272, 274, 318, 323, 333, 339, 361–365, 369, 370, 372, 374, 376–378, 380, 381, 383–386, 389–392, 397, 403, 404, 406, 407, 414–415, 419, 254; 540/596, 598, 601, 602, 603; 544/3, 8, 58.2, 54–56, 63, 68, 88, 98, 120, 123, 131, 132, 139, 143, 179, 182, 238, 295, 296, 310, 315–320, 324, 328, 331, 333, 357, 405; 546/193, 194, 201, 256, 273; 548/125, 127–136, 142–144, 181, 213, 214, 225–231, 233, 235, 236, 251–255, 263–267, 269, 301, 307, 309, 311–313, 336, 361, 362, 364, 374, 466–468

[56] References Cited

U.S. PATENT DOCUMENTS

| | | | |
|---|---|---|---|
| 3,322,786 | 5/1967 | Sletzinger | 548/371 |
| 4,126,620 | 11/1978 | Bell et al. | 514/182 |
| 4,144,338 | 3/1979 | Bolhofer | 544/182 |
| 4,148,895 | 4/1979 | Luttrell | 514/234 |
| 4,181,665 | 1/1980 | McCall | 544/182 |
| 4,258,185 | 3/1981 | Nakao | 544/114 |
| 4,479,962 | 10/1984 | Wiedemann | 514/406 |
| 4,499,181 | 2/1985 | Watanabe | 430/558 |

FOREIGN PATENT DOCUMENTS

| | | |
|---|---|---|
| 0052442 | 5/1982 | European Pat. Off. . |
| 0085227 | 8/1983 | European Pat. Off. . |
| 0122494 | 10/1984 | European Pat. Off. . |
| 0129791 | 1/1985 | European Pat. Off. . |
| 2845220 | 4/1980 | Fed. Rep. of Germany . |
| 2530246 | 1/1984 | France . |

OTHER PUBLICATIONS

Merck, Chem. Abs., 65, 20103(b), 1966.
Wentrup et al., "Synthesis of 1-Azaazulene and Benz-[a]azulene by Carbene . . . ", J. Am. Chem. Soc., 106, 3705–6, (1984).
Mullock et al., "Synthetic Uses of Polyphosphoric Acid and Its Ethyl . . . ", J. Chem. Soc., (c) 1970, 829–33.
Abstract: Japanese Patent Publication 58-8016(A), pub. 18 Jan. 1983.

Primary Examiner—Mark L. Berch
Attorney, Agent, or Firm—Felfe & Lynch

[57] ABSTRACT

The present invention provides indole derivatives of the general formula:

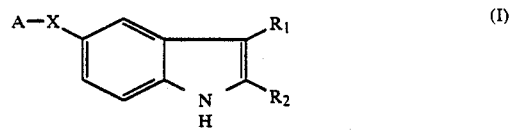

wherein $R_1$ is a hydrogen atom or an alkyl, alkenyl, cycloalkyl, cycloalkenyl, carboxyl, cyano, alkylcarbonyl, alkoxycarbonyl, aminocarbonyl, alkylaminocarbonyl, dialkylaminocarbonyl or aryl radical, $R_2$ is a hydrogen atom or an alkyl, trihalogenomethyl, hydroxyl, cycloalkyl, cyano, carboxyl, alkoxycarbonyl, alkylcarbonyl, aminocarbonyl, alkylaminocarbonyl or dialk- (Abstract continued on next page.)

ylaminocarbonyl radical; R₂ is a heterocyclic five-membered ring containing 1 to 4 heteroatoms or a heterocyclic six-membered ring containing 1 to 5 heteroatoms, the heteroatoms of the five- and six-membered rings being the same or different and being nitrogen, oxygen or sulphur and one or more of the nitrogen atoms optionally carrying an oxygen atom, the said five- and six-membered rings optionally being substituted by one or more alkyl, alkoxy, alkylthio, oxo, hydroxyl, nitro, amino, halogen or cyano groups; or R₂ is

(II)

the tautomers thereof and the physiologically acceptable salts thereof with inorganic and organic acids.

The present invention also provides processes for the preparation of these compounds and pharmaceutical compositions containing them.

Furthermore, the present invention provides intermediates of the general formula:

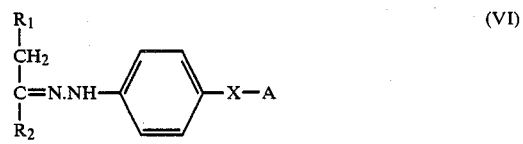
(VI)

in which $R_1$, $R_2$, A and X have the same meanings as above, and processes for the preparation of these intermediates.

18 Claims, No Drawings

HETEROCYCLIC-SUBSTITUTED INDOLES AND PHARMACEUTICAL COMPOSITIONS CONTAINING THEM

The present invention is concerned with new heterocyclic-substituted indoles, with intermediates and processes for the preparation thereof and with pharmaceutical compositions containing them.

The new heterocyclic-substituted indoles according to the present invention are compounds of the general formula:

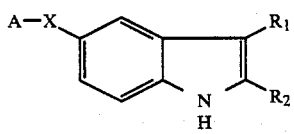

wherein $R_1$ is a hydrogen atom or an alkyl, alkenyl, cycloalkyl, cycloalkenyl, carboxyl, cyano, alkylcarbonyl, alkoxycarbonyl, aminocarbonyl, alkylaminocarbonyl, dialkylaminocarbonyl or aryl radical, $R_2$ is a hydrogen atom, an alkyl, trihalogenomethyl, hydroxyl, cycloalkyl, cyano, carboxyl, alkoxycarbonyl, alkycarbonyl, aminocarbonyl, alkylaminocarbonyl or dialkylaminocarbonyl radical; or $R_2$ is a heterocyclic five-membered ring containing 1 to 4 heteroatoms or a heterocyclic six-membered ring containing 1 to 5 heteroatoms, the heteroatoms in the said five- and six-membered rings being the same or different and being nitrogen, oxygen or sulphur, one or more of the nitrogen atoms optionally carrying an oxygen atom, the said five- and six-membered rings being optionally substituted by one or more alkyl, alkoxy, alkylthio, oxo, hydroxyl, nitro, amino, halogeno or cyano radicals; or $R_2$ is a phenyl radical of the general formula:

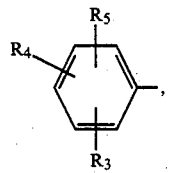

wherein $R_3$, $R_4$ and $R_5$ are the same or different and each signifies a hydrogen atom, an alkanesulphonyloxy, trifluoromethanesulphonyloxy, alkanesulphonylamino, trifluoromethanesulphonylamino, N-alkyl-alkanesulphonylamino, N-alkyl-trifluoromethanesulphonylamino, alkylsulphenylmethyl, alkylsulphinylmethyl or alkylsulphonylmethyl radical, a carbonyl group substituted by a hydroxyl, alkoxy, amino, alkylamino or dialkylamino radical, a sulphonyl group substituted by an amino, alkylamino, dialkylamino or cyclic imino group, whereby a methylene group in the 4-position can be replaced by a sulphur or oxygen atom, an alkylcarbonylamino, aminocarbonylamino or alkylaminocarbonylamino radical, an alkylthio, alkylsulphinyl or alkylsulphonyl radical, a nitro, halogen, amino, hydroxyl, alkyl, alkoxy, alkenyloxy, alkynyloxy, cyanoalkoxy, carboxyalkoxy, alkoxycarbonylalkoxy, dialkylamino, 1-imidazolyl, trifluoromethyl or cyano radical, A is a heterocyclic five-membered ring containing 1 to 4 heteroatoms or a heterocyclic six-membered ring containing 1 to 5 heteroatoms, whereby the heteroatoms in the said five- and six-membered rings can be the same or different and being nitrogen, oxygen or sulphur atoms and the said five- and six-membered rings being optionally substituted by one or more alkyl, alkoxy, alkoxyalkyl, alkylthio, hydroxyl, hydroxyalkyl, oxo, amino, halogen, aminocarbonyl or cyano radicals and X is a valency bond or a $C_1$-$C_4$ alkylene or a vinylene radical; the tautomers thereof and the physiologically acceptable salts thereof with inorganic and organic acids.

When the compounds of general formula (I) contain an asymmetric carbon atom, the present invention also includes the optically-active forms and racemic mixtures of these compounds.

The new compounds according to the present invention have valuable pharmacological properties and, in particular, they increase the strength of the heart and/or lower the blood pressure and/or influence the thrombocyte function and improve the microcirculation.

When $R_1$ in compounds of general formula (I) signifies a hydrogen atom, an alkyl, alkenyl, cycloalkyl, cycloalkenyl, cyano, alkylcarbonyl, alkoxycarbonyl, aminocarbonyl, alkylaminocarbonyl, dialkylaminocarbonyl or aryl radical, then the above-mentioned alkyl and alkoxy radicals and cycloalkyl and cycloalkenyl radicals can contain 1 to 7 and 3 to 7 carbon atoms, respectively, and preferably 1 to 5 and 3 to 6 carbon atoms, respectively. Besides the hydrogen atom, the cyano group and the phenyl radical, there are also preferred, for example, the methyl, ethyl, propyl, isopropyl, butyl, allyl, cyclopropyl, cyclopentyl, cyclohexyl, cyclopentenyl, acetyl, propionyl, methoxycarbonyl, ethoxycarbonyl, aminocarbonyl, methylaminocarbonyl and dimethylaminocarbonyl radicals.

When $R_2$ is an alkyl, trihalogenomethyl, cycloalkyl, cycloalkenyl, cyano, carboxyl, alkylcarbonyl, alkoxycarbonyl, alkylaminocarbonyl or dialkylaminocarbonyl radical, then the above-mentioned alkyl and cycloalkyl radicals contain 1 to 7 and 3 to 7 carbon atoms, respectively. Preferred radicals for $R_2$ include methyl, ethyl, isopropyl, n-butyl, trifluoromethyl, cyclopentyl, cyclohexyl, cyclopentenyl, cyclohexenyl, hydroxyl, cyano, carboxyl, acetyl, propionyl, methoxycarbonyl, ethoxycarbonyl, methylaminocarbonyl and dimethylaminocarbonyl radicals.

When $R_2$ is a heterocyclic five-membered ring with 1 to 4 heteroatoms or a heterocyclic six-membered ring with 1 to 5 heteroatoms, the heteroatoms in the said five- and six-membered rings being the same or different and being nitrogen, oxygen or sulphur and one or more nitrogen atoms optionally carrying an oxygen atom, then $R_2$ is preferably a pyrrole, furan, thiophene, pyrazole, imidazole, thiazole, oxazole, triazole, tetrazole, thiadiazole, oxadiazole, pyrazine, N,N-dioxypyrazine, pyrimidine, N,N-dioxypyrimidine, pyridazine, oxazine, thiazine, triazine, tetrazine, pyridyl or N-oxypyridyl radical.

Alkyl, alkoxy and alkylthio substituents in the heterocyclic five- and six-membered rings can contain up to 6 and preferably up to 4 carbon atoms, the methyl, ehtyl, methoxy, ethoxy, methylthio and ethylthio radicals being preferred. By halogen is to be understood fluorine, chlorine or bromine, chloring being preferred.

When $R_2$ is a phenyl radical of general formula (II), then the alkyl moiety of the substituents $R_3$, $R_4$ and $R_5$ can contain up to 5 and preferably up to 4 carbon atoms. Preferred substituents in this sense include methanesulphonyloxy, ethanesulphonyloxy, n-propanesulphonyloxy, isopropanesulphonyloxy, trifluoromethanesulphonyloxy, methylsulphenylmethyl, ethylsulphenylmethyl, n-propylsulphenylmethyl, methylsulphinylmethyl, ethylsulphinylmethyl, n-propylsulphinylmethyl, methylsulphonylmethyl, ethylsulphonylmethyl, n-propylsulphonylmethyl, methanesulphonylamino, ethanesulphonylamino, n-propanesulphonylamino, trifluoromethanesulphonylamino, N-methyl-methanesulphonylamino, N-ethyl-methanesulphonylamino, N-methyl-ethanesulphonylamino, N-ethyl-ethanesulphonylamino, N-isopropylethanesulphonylamino, N-methyl-n-propanesulphonylamino, N-n-propyl-n-propanesulphonylamino, N-methyl-trifluoromethanesulphonylamino, N-ethyltrifluoromethanesulphonylamino, N-isopropyl-trifluoromethanesulphonylamino, methoxycarbonyl, propoxycarbonyl, isopropoxycarbonyl, methylaminocarbonyl, ethylaminocarbonyl, dimethylaminocarbonyl, di-n-propylaminocarbonyl, N-methyl-ethylaminocarbonyl, trifluoromethyl, methylaminosulphonyl, ethylaminosulphonyl, n-propylaminosulphonyl, n-butylaminosulphonyl, n-pentylaminosulphonyl, dimethylaminosulphonyl, diethylaminosulphonyl, di-n-propylaminosulphonyl, N-methylisopropylaminosulphonyl, acetylamino, propionylamino, methylaminocarbonylamino, ethylaminocarbonylamino, propylaminocarbonylamino, methyl, ethyl, propyl, methoxy, ethoxy, propoxy, allyloxy, but-2-enyloxy, but3-enyloxy, pent-2-eloxy, propargyloxy, but-2-ynyloxy, but-3-ynyloxy, cyanomethoxy, cyanoethoxy, methoxycarbonylmethoxy, methoxycarbonylethoxy, methylthio, ethylthio, methylsulphinyl, ethylsulphinyl, methylsulphonyl and ethylsulphonyl radicals.

In the case of sulphonyl groups which can be substituted by cyclic imino groups, they are preferably morpholino-, pyrrolidino-, piperidino- and hexamethyleneiminosulphonyl radicals.

$R_3$ is especially preferably a hydrogen atom, an alkylsulphonyloxy, trifluoromethylsulphonyloxy, alkylsulphenylmethyl, alkylsulphinylmethyl, alkylsulphonylmethyl, alkylsulphonylamino, N-alkyl-alkylsulphonylamino, trifluoromethylsulphonylamino or N-alkyl-trifluoromethylsulphonylamino radical, a carbonyl group substituted by a hydroxyl, alkoxy, amino, alkylamino or dialkylamino radical or a sulphonyl group substituted by an amino, dialkylamino or morpholino radical, each of the above-mentioned alkyl moieties containing 1 or 2 carbon atoms, a nitro or cyano group or an alkylaminosulphonyl radical containing up to 4 carbon atoms, an alkylcarbonylamino, aminocarbonylamino or N-alkyl-aminocarbonylamino radical, an alkylthio, alkylsulphinyl or alkylsulphonyl radical, wherein each of the above-mentioned alkyl moieties contain 1 or 2 carbon atoms, a halogen amino, hydroxyl, dialkylamino, alkyl, alkoxy, alkenyloxy or alkynyloxy radical preferably with up to 3 carbon atoms, a cyanomethyl or methoxycarbonylmethoxy radical, a trifluoromethyl radical or a 1-imidazolyl radical, $R_4$ is preferably a hydrogen atom, an alkyl radical containing up to 3 carbon atoms, an alkoxy or dialkylamino radical containing 1 or 2 carbon atoms in the alkyl moiety or a halogen atom, and $R_5$ is a hydrogen atom or a methoxy radical.

The phenyl radical can contain 1 to 3 of the said substituents.

Preferred mono-substituted phenyl compounds include the hydroxyl, $C_1$-$C_3$ alkyl, $C_1$-$C_3$ alkoxy, allyloxy, propargyloxy, cyanomethoxy, methoxycarbonylmethoxy, halogen, nitro, cyano, aminocarbonyl, methoxycarbonyl, amino, $C_1$-$C_3$ dialkylamino, $C_1$-$C_3$ alkylthio, $C_1$-$C_3$ alkylsulphinyl, $C_1$-$C_3$ alkylsulphonyl, $C_1$-$C_3$ alkylsulphonyloxy and the 1-imidazolyl compounds, the substituent being in the 2-, 3- or 4-position.

Preferred disubstituted phenyl compounds contain as substituents alkanesulphonyloxy, trifluoromethylsulphonyloxy, alkylsulphenylmethyl, alkylsulphinylmethyl, alkylsulphonylmethyl, alkylsulphonylamino, N-alkylalkylsulphonylamino, trifluoromethylsulphonylamino or N-alkyl-trifluoromethylsulphonylamino radicals, a carbonyl group substituted by a hydroxyl, alkoxy, amino, alkylamino or dialkylamino radical or a sulphonyl group substituted by an amino, dialkylamino or morpholino radical, an alkylaminosulphonyl, alkylcarbonylamino, aminocarbonylamino or N-alkyl-aminocarbonylamino radical, a hydroxyl, alkyl, alkoxy, allyloxy, propargyloxy, cyanomethoxy, methoxycarbonylmethoxy, cyano, halogen, nitro, amino, dialkylamino, alkylthio, alkylsulphinyl, alkylsulphonyl or 1-imidazolyl radical, whereby the two substituents can be the same or different and are in the 2,3-, 2,4-, 2,5-, 2,6-, 3,4- or 3,5-position but preferably in the 2,4- 2,5- or 3,4-position and the above-mentioned alkyl moieties, alone or in combination with other residues, can contain up to 3 carbon atoms.

A preferred trisubstituted phenyl radical is the 3,4,5-trimethoxyphenyl radical.

When A is a heterocyclic five- or six-membered ring with 1 to 4 and 1 to 5, respectively, identical or different heteroatoms, such as oxygen, sulphur or nitrogen, then it is preferably a pyrrole, pyrazole, imidazole, thiazole, oxazole, triazole, thiadiazole, oxadiazole, pyrazine, pyrimidine, pyridazine, oxazine, thiazine, triazine, tetrazine or pyridine radical which is optionally substituted by one or more alkyl, alkoxy, alkoxyalkyl, alkylthio, hydroxyl, hydroxyalkyl, amino, aminocarbonyl, halogen or cyano radicals. Preferred radicals include the 3-oxo-2,3-dihydro-6-pyridazinyl, 5-alkyl-3-oxo-2,3-dihydro-6-pyridazinyl, 3-oxo-2,3,4,5-tetrahydro-6-pyridazinyl, 5-alkyl-3-oxo-2,3,4,5-tetrahydro-6-pyridazinyl, 5-hydroxyalkyl-3-oxo-2,3,4,5-tetrahydro-6-pyridazinyl, 3-cyano-6-alkyl-2-oxo-1,2-dihydro-5-pyridinyl, 3-aminocarbonyl-6-alkyl-2oxo-1,2-dihydro-5-pyridinyl, 6-alkyl-2-oxo-1,2-dihydro-5-pyridinyl, 3-amino-2-oxo-1,2-dihydro-5-pyridinyl, 3-amino-6-alkyl-2-oxo-1,2-dihydro-5-pyridinyl, 3-hydroxy-6-alkyl-2-oxo-1,2-dihydro-5-pyridinyl, 3-oxo-2H-3,4-dihydro-1,4-thiazin-6-yl, 6-oxo-1,6-dihydro-1,2,4-triazin-3-yl, 6-oxo-1,4,5,6-tetrahydro-1,2,4-triazin-3-yl, 5-oxo-4,5-dihydro-6H-1,3,4-oxadiazin-2-yl, 5-oxo-4,5-dihydro-6H-1,3,4-thiadiazin-2-yl, 3-oxo-2,3-dihydro-1,2,4-triazin-6-yl, 3-oxo-2,3,4,5-tetrahydro-1,2,4-triazin-6-yl, 2-oxo-2,3-dihydro-6H-1,3,4-oxadiazin-5-yl, 2-oxo-2,3-dihydro-6H-1,3,4-thiadiazin-5-yl, 5-alkyl-3-3-oxo-1,3,4,5-tetrahydro-1,2,4,-triazin-6-yl, 2-oxo-1,2-dihydro-5-pyrimidinyl, 4-alkyl-2-oxo-1,2-dihydro-5-pyrimidinyl, 2-oxo-1,2-dihydro-5-pyrazinyl, 3-alkyl-2-oxo-1,2-dihydro-5-pyrazinyl, 6-alkyl-2-oxo-1,2-dihydro-5-pyrazinyl, 4,4-dialkyl-5-oxo-4,5-dihydro-3-pyrazolyl, 2-oxo-4-pyrrolidinyl, 3-alkyl-2-oxo-4-pyrrolidinyl, 5-oxo-4,5-dihydro-1,2,4-triazol-3-yl, 4-alkyl-5-oxo-4,5-dihydro-1,2,4-triazol-3-yl, 2-oxo-2,3-dihydro-4(5)-imidazolyl and 5(4)-alkyl-2-oxo-2,3-dihydro-4(5)-imidazolyl radicals.

X is preferably a valency bond or a vinylene or ethylene radical.

Especially preferred compounds of general formula (I) are those in which $R_1$ is a hydrogen atom or a methyl, ethyl, isopropyl, n-butyl, allyl, cyclohexyl, cyclopentenyl, cyano, ethoxycarbonyl or phenyl radical, $R_2$ is a methyl, ehtyl, isopropyl, trifluoromethyl, cyclopentyl, cyano, acetyl, carboxyl, methoxycarbonyl, ethoxycarbonyl, methylaminocarbonyl or dimethylaminocarbonyl radical, or $R_2$ is a pyrrole, furan, thiophene, pyrazole, imidazole, thiazole, oxazole, triazole, tetrazole, thiadiazole, oxadiazole, pyridine, N-oxypyridine, pyrazine, N,N-dioxypyrazine, pyrimidine, N,N-dioxypyrimidine, pyridazine, oxazine, thiazine, triazine or tetrazine radical, as well as the methyl, ethyl, methoxy, ethoxy, methylthio, ethylthio and chlorine substituted derivatives thereof, or $R_2$ is a phenyl radical of general formula (II), in which $R_3$ is a hydrogen atom, a methanesulphonyloxy, trifluoromethanesulphonyloxy, methanesulphonylamino, trifluoromethanesulphonylamino, N-methyl-methanesulphonylamino, N-methyl-trifluoromethanesulphonylamino, methylsulphenylamino, methylsulphinylmethyl, methylsulphonylmethyl, aminocarbonyl, aminosulphonyl, methylaminosulphonyl, dimethylaminosulphonyl, acetylamino, methylthio, methylsulphonyl, hydroxyl, methyl, methoxy, propargyloxy, cyanomethoxy, methoxycarbonylmethoxy, cyano, chlorine, nitro, amino, dimethylamino, trifluoromethyl or 1-imidazolyl radical, $R_4$ is a hydrogen atom or chlorine atom or a methyl, methoxy or dimethylamino radical, $R_5$ is a hydrogen atom or a methoxy radical, A is a 3-oxo-2,3,4,5-tetrahydro-6-pyridazinyl, 5-methyl-3-oxo-2,3,4,5-tetrahydro-6-pyridazinyl, 5-hydroxymethyl-3-oxo-2,3,4,5-tetrahydro-6-pyridazinyl, 3-cyano-6-methyl-2-oxo-1,2-dihydro-5-pyridinyl, 3-aminocarbonyl-6-methyl-2-oxo-1,2-dihydro-5-pyridinyl, 3-oxo-2,3,4,5-tetrahydro-1,2,4-triazin-6-yl, 2-oxo-4,5-dihydro-6H-1,3,4-oxadiazin-5-yl, 6-oxo-1,4,5,6-tetrahydro-1,2,4-triazin-3-yl, 5-oxo-4,5-dihydro-6H-1,3,4-oxadiazin-2-yl, 2-oxo-1,2-dihydro-5-pyrimidinyl, 2-oxo-1,2-dihydro-5-pyrazinyl, 4,4-dimethyl-5-oxo-4,5-dihydro-3-pyrazole, 2-oxo-4-pyrrolidinyl, 4-methyl-5-oxo-4,5-dihydro-1,2,4-triazol-3-yl or 5(4)-methyl-2-oxo-2,3-dihydro-4(5)imidazolyl radical and X is a valency bond, a vinylene or ethylene radical.

The compounds of general formula (I) can be prepared by processes known from the literature for the synthesis of indoles. In this regard, see:

(a) P. L. Julian, E. W. Meyer and H. C. Printy, in R. C. Elderfield (ed.), Heterocyclic Compounds, Vol. 1, pp. 1–231, pub.; John Wiley & Sons, New York, 1952

(b) R. K. Brown, in W. J. Houlihan (ed.), Hetrocyclic Compounds, Vol. 25, Part I, pp. 227–537, pub. John Wiley & Sons, New York, 1972.

The synthetic route shown in the following scheme 1 is especially advantageous:

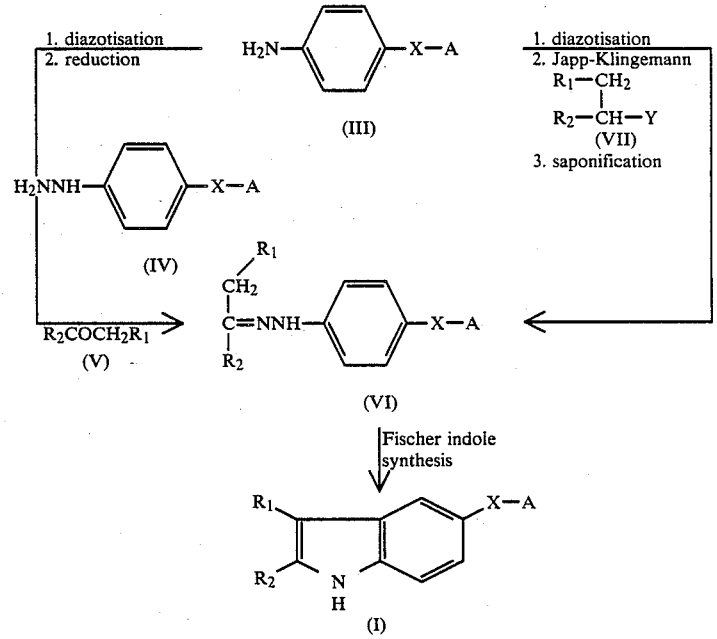

As can be seen from scheme 1, the compounds of general formula (III), which are known from the literature or can be prepared by processes known from the literature, in which X and A have the above-given meanings, can be diazotised and the diazonium salt reduced to the hydrazine (IV). By reaction of these hydrazines with compounds of the general formula:

$$R_2COCH_2R_1 \qquad (V),$$

in which $R_1$ and $R_2$ have the above-given meanings, there are obtained hydrazones (VI) which can be cyclised by a Fischer indole synthesis to give compounds of general formula (I). On the other hand, the hydrazones of general formula (VI) can also be obtained by reacting the diazonium salt of the amines (III) in a Japp-Klingemann reaction with compounds of the general formula:

in which $R_1$ and $R_2$ have the above-given meaning and Y is a residue activating the methine group. This residue can be, for example, an aldehyde, ketone, ester, carboxylic acid or nitrile group. The azo compounds obtained as intermediates in the reaction mixture are, without isolation, saponified directly to give the hydrazones.

The compounds of general formula (VI) are new and are also the subject of the present invention.

The diazotisation of the amines (III) is preferably carried out under neutral or acidic conditions in a polar solvent, such as water, methanol, ethanol, glacial acetic acid, hydrochloric acid, sulphuric acid or phosphoric acid, at a temperature of from −70° to +50° C. and preferably of from −5° to +10° C. For the diazotisation, there are mainly used inorganic salts or organic esters of nitrous acid, for example sodium or potassium nitrite or amyl nitrite.

The reduction of the diazonioum salts is preponderantly carried out in the above-mentioned solvents in which the diazotisation is carried out at a temperature of from −50° C. to the boiling point of the solvent but preferably at a temperature of from 0° to 80° C. The reducing agent can be, for example, an alkali metal sulphite, sulphur dioxide, a dithionite, stannous chloride, zinc dust, iron, sodium amalgam, triphenylphosphine or an endiol but an electrochemical reduction can also be used.

The reaction of the hydrazines with compounds of the general formula (V) can be carried out in a solvent, such as water, alcohol, benzene, toluene, dioxan, dimethylformamide, diethyl ether or tetrahydrofuran, at a temperature of from −80° C. to the boiling point of the solvent used. The addition of an inorganic or organic acid, such as hydrochloric acid, sulphuric acid, phosphoric acid or acetic acid, is also advantageous.

The Japp-Klingemann reaction is advantageously carried out in the solvents in which the above-described diazotisation can be carried out. These are, in particular, water, methanol, ethanol, glacial acetic acid, hydrochloric acid, sulphuric acid or phosphoric acid, the temperature used being from −50° to +80° C. and preferably from 0° to 25° C. The subsequent saponification can be carried out thermally or after the addition of a base or acid, for example aqueous sodium or potassium hydroxide solution, hydrochloric acid, sulphuric acid, phosphoric acid or glacial acetic acid, at a temperature of up to the boiling point of the solvent used.

The Fischer indole synthesis of the hydrazones (VI) is carried out without a solvent or in a solvent, such as alcohol, nitrobenzene, acetic acid, xylene, cumol or toluene, thermally or in the presence of an acidic catalyst which can, however, also be the solvent, for example with hydrochloric acid, sulphuric acid, phosphoric acid, polyphosphoric acid, glacial acetic acid, formic acid, zinc chloride, boron trifluoride, a cation exchanger, sulphosalicylic acid or a polyphosphate ester, at a temperature of from 0° C. to the boiling point of the solvent used.

The hydrazones of general formula (VI) can possibly be prepared also from amines (III) via the sydnones (X) according to scheme 2:

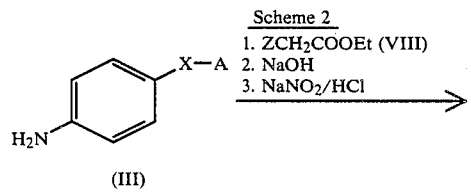

(III)

Scheme 2
1. ZCH₂COOEt (VIII)
2. NaOH
3. NaNO₂/HCl

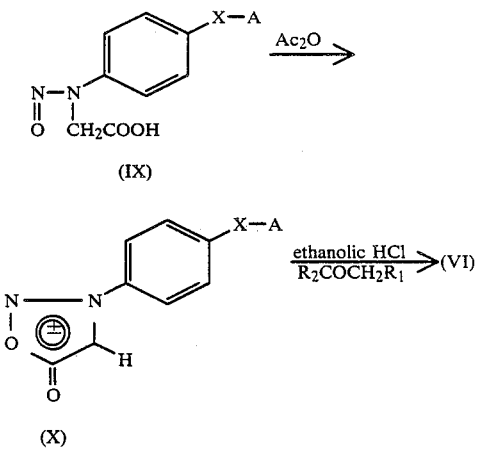

The reaction of amines (III) with halogenoacetic acid esters (VIII), in which Z is a halogen atom, such as fluorine, chlorine, bromine or iodine but preferably bromine, is advantageously carried out in a polar or non-polar solvent, for example methylene chloride, toluene, dioxan, alcohols or dimethylformamide, at a temperature of from −50° C. to the boiling point of the solvent and preferably of from 25° to 100° C.

The esters thus obtained can ve saponified according to well known processes, for example with an inorganic base, such as sodium or potassium hydroxide, sodium hydrogen carbonate or potassium hydrogen carbonate, in protic solvents, such as water or an alcohol, or with an inorganic or organic acid, such as hydrochloric acid, sulphuric acid, glacial acetic acid, phosphoric acid or polyphosphoric acid, possibly with the addition of a solvent, such as water or alcohol.

The nitrosation of the acids obtained to give compounds of general formula (IX) is preferably carried out under neutral or acidic conditions in a polar solvent, such as water, methanol, ethanol, glacial acetic acid, hydrochloric acid, sulphuric acid or phosphoric acid, at a temperature of from −70° to +50° C. but preferably of from −5° to +10° C. For the nitrosation, thereare mainly used inorganic salts or organic esters of nitrous acid, for example sodium or potassium nitrite or amyl nitrite.

The reaction of the N-nitroso-carboxylic acids (IX) to give the sydnones (X) takes place in an inert solvent, for example dioxan, diethyl ether, tetrahydrofuran or toluene, with a water-removing agent, for example acetic anhydride, propionic acid anhydride, sulphuric acid, phosphorus pentoxide, phosphorus pentachloride or phosphorus trichloride, at a temperature of from −50° C. to the boiling point of the solvent but advantageously of from 25° to 100° C.

The sydones (X) can be decomposed under acidic conditions to give the hydrazines (IV) which are taken up in situ with the ketones (V) to give the hydrazones (VI). As acids for the saponification of the sydnones, there can be used an inorganic acid, for example, hydrochloric acid, sulphuric acid, phosphoric acid or polyphosphoric acid, or an organic acid, such as glacial acetic acid, at a temperature of from −70° to +100° C. and preferably of from 0° to 70° C.

Compounds of general formula (I) can also be subsequently converted into other compounds of general formula (I). This applies, for example, for:

(a) The oxidation of a five- or six-membered ring with one or more nitrogen atoms to give the corresponding N-oxides. The oxidation is preferably carried out with one or more equivalents of the oxidation agent used, for example with hydrogen peroxide in glacial acetic acid, trifluoroacetic acid or in formic acid at 20° to 100° C. or in acetone at 0° to 60° C., or with a per acid, such as performic acid or m-chloroperbenzoic acid, in glacial acetic acid, trifluoroacetic acid, methylene chloride or chloroform, at a temperature of from 0° to 60° C.

(b) The preparation of compounds of general formula (I), in which $R_2$ is a radical of general formula (II) and $R_3$ is an alkylsulphinyl, alkylsulphonyl, alkylsulphinylmethyl or alkylsulphonylmethyl radical, by subsequent oxidation of a compound of the general formula:

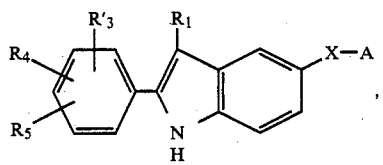

(XI)

wherein $R_1$, $R_4$, $R_5$, A and X have the above-given meanings and $R'_3$ is an alkylthio or alkylsulphenylmethyl radical with, in each case, up to 3 carbon atoms in the alkyl moiety. The oxidation is preferably carried out in a solvent or solvent mixture, for example water, water/pyridine, acetone, glacial acetic acid, dilute sulphuric acid or trifluoroacetic acid, depending upon the oxidation agent used, preferably at a temperature of from −80° to +100° C.

For the preparation of an alkylsulphinyl or alkylsulphinylmethyl compound of general fomula (I), the oxidation is preferably carried out with an equivalent of the oxidation agent used, for example with hydrogen peroxide in glacial acetic acid, trifluoroacetic acid or formic acid at 0° to 20° C. or in acetone at 0° to 60° C., with a per acid, such as performic acid, in glacial acetic acid or trifluoroacetic acid, at 0° to 50° C. or with m-chloroperbenzoic acid in methylene chloride or chloroform at −20° to +60° C., with sodium metaperiodate in aqueous methanol or ethanol at −15° to +25° C., with bromine in glacial acetic acid or aqueous acetic acid, with N-bromosuccinimide in ethanol, with tert.-butyl hypochloride in methanol at −80° to −30° C., with iodobenzodichloride in aqueous pyridine at 0° to 50° C., with nitric acid in glacial acetic acid at 0° to 20° C., with chromic acid in glaical acetic acid or in acetone at 0° to 20° C. or with sulphuryl chloride in methylene chloride at −70° C., the thioether chlorine complex hereby obtained being preferably hydrolysed with aqueous ethanol.

For the preparation of an alkylsulphonyl or alkylsulphonylmethyl compound of general formula (I), the oxidation is preferably carried out with one or with two or more equivalents of the oxidation agent used, for example hydrogen peroxide in glacial acetic acid, trifluoroacetic acid or in formic acid at 20° to 100° C. or in acetone at 0° to 60° C., with a per acid, such as performic acid or m-chloroperbenzoic acid, in glacial acetic acid, trifluoroacetic acid, methylene chloride or chloroform, at a temperature of from 0° to 60° C., with nitric acid in glacial acetic acid at 0° to 20° C. or with chromic acid or with potassium permanganate in glacial acetic acid, water/sulphuric acid or in acetone at 0° to 20° C.

(c) The preparation of compounds of general formula (I), wherein $R_2$ is a radical of general formula (II) and $R_3$ is an alkanesulphonyloxy, trifluoromethanesulphonyloxy, alkanesulphonylamino, N-alkyl-alkanesulphonylamino, trifluoromethanesulphonylamino or N-alkyl-trifluoromethanesulphonylamino radical, by the subsequent reaction of a compound of the general formula:

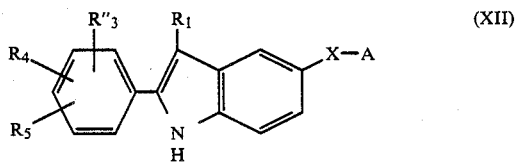

(XII)

wherein $R_1$, $R_4$, $R_5$, A and X have the above-given meanings and $R''_3$ is a hydroxyl, amino or N-alkylamino radical with up to 3 carbon atoms in the alkyl moiety, with a sulphonic acid of the general formula:

$R_6$—SO$_2$OH  (XIII)

wherein $R_6$ is an alkyl radical containing up to 3 carbon atoms or a trifluoromethyl radical, in the presence of a water-removing agent and/or of an agent activating the acid or the amine or with a reactive derivative thereof.

The reaction is preferably carried out in a solvent or solvent mixture, such as methylene chloride, diethyl ether, tetrahydrofuran, dioxan or benzene, optionally in the presence of an acid-binding agent, such as sodium carbonate, triethylamine or pyridine, whereby the latter two can also simultaneously serve as solvent, in the presence of an agent activating the acid or removing water, such as thionyl chloride or phosphorus pentachloride, but preferably with a reactive derivative of a compound of general formula (XIII), for example with an anhydride or halide thereof, such as methanesulphonic acid chloride or ethanesulphonic acid chloride, preferably at a temperature of from 0° to 100° C., for example at a temperature of from ambient temperature to 50° C.

(d) The preparation of compounds of general formula (I), wherein $R_2$ is a radical of general formula (II) and $R_3$ is a carbonyl or sulphonyl group substituted by an amino, alkylamino, dialkylamino or hydrazino radical, by the subsequent reaction of a compound of the general formula:

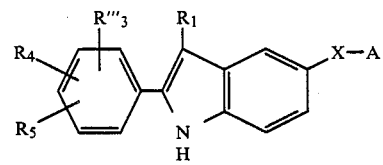

(XIV)

wherein $R_1$, $R_4$, $R_5$, A and X have the above-given meanings and $R'''_3$ is a carboxyl or hydroxysulphonyl group, or a reactive derivative thereof, for example an ester or acid chloride, with hydrazine or an amine of the general formula:

$R_7$—NH—$R_8$  (XV), wherein $R_7$ and $R_8$ can be the same or different and represent hydrogen atoms or alkyl radicals containing up to 5 carbon atoms, or with a reactive derivative thereof if $R'''_3$ is a carboxyl or hydroxysulphonyl radical.

The reaction is preferably carried out in a solvent, such as methylene chloride, ethanol, chloroform, carbon tetrachloride, acetonitrile or dimethylformamide, optionally in the presence of an acid-activating agent or of a water-removing agent, for example, in the presence of ethyl chloroformate, thionyl chloride, phosphorus trichloride, phosphorus pentoxide, N,N'-dicyclohexylcarbodiimide/N-hydroxysuccinimide, N,N'-thionyldiimidazole or triphenylphosphine/carbon tetrachloride, or of an agent activating the hydrazino or amino group, for example phosphorus trichloride, and optionally in the presence of an inorganic base, such as sodium carbonate, or a tertiary organic base, such as triethylamine of pyridine, which can simultaneously serve as a solvent, at a temperature of from $-25°$ to $+250°$ C. but preferably at a temperature of from $-10°$ C. to the boiling point of the solvent used. Furthermore, water formed during the reaction can be removed by azeotropic distillation, for example by heating with toluene on a water separator, or by the addition of a drying agent, such as anhydrous magnesium sulphate or of a molecular sieve.

However, the reaction can be carried out especially advantageously with an appropriate halide, for example the carboxylic acid or sulphonic acid chloride, and hydrazine or an appropriate amine, whereby these can simultaneously serve as solvent, at a temperature of from 0° to 50° C.

(e) The preparation of compounds of general formula (I), in which $R_1$ is a cyano group, by subsequent reaction of a compound of general formula (I), in which $R_2$, A and X have the above-given meanings and $R_1$ is a hydrogen atom, with N-carbonylsulphamoyl chloride, which can also be called chlorosulphonyl isocyanate, in an appropriate solvent according to known processes (see Chem. Ber., 100, 2719/1967; Synthesis, 1978, 374 and J. Chem. Soc., Perkin I, 1978, 1117).

The reaction is preferably carried out in a solvent which is inert under the reaction conditions, for example water, methanol, ethanol, n-butanol, dioxan, acetonitrile, nitromethane, pyridine, dimethylformamide or methylene chloride, optionally in the presence of an acid-binding agent. The reaction is carried out with ice cooling, at ambient temperature or with heating, optionally under a protective gas atmosphere.

(f) The preparation of compounds of general formula (I), in which $R_1$ or $R_2$ is a carboxyl, alkoxycarbonyl or aminocarbonyl radical or $R_2$ is a radical of general formula (II) and $R_3$ is a carboxyl, alkoxycarbonyl, aminocarbonyl, alkoxycarbonylalkoxy or carboxyalkoxy radical, by subsequent alcoholysis and/or hydrolysis of compounds of general formula (I), in which $R_1$ and $R_2$ signify a cyano group or $R_2$ is a radical of general formula (II) and $R_3$ is a cyano or cyanoalkoxy radical.

The subsequent alcoholysis and/or hydrolysis is preferably carried out either in the presence of an acid, such as hydrochloric acid, sulphuric acid, phosphoric acid or trichloroacetic acid, or in the presence of a base, such as sodium or potassium hydroxide, in an appropriate solvent, such as water, water/methanol, ethanol, water/ethanol, water/isopropanol and water/dioxan, at a temperature of from $-10°$ to $+120°$ C., for example at a temperature of from ambient temperature to the boiling temperature of the reaction mixture.

Furthermore, if desired, the compounds obtained of general formula (I) can be converted into their physiologically acceptable acid-addition salts with inorganic or organic acids. As acids for this purpose, there can be used, for example, hydrochloric acid, hydrobromic acid, sulphuric acid, phosphoric acid, fumaric acid, succinic acid, tartaric acid, citric acid, lactic acid, maleic acid or methanesulphonic acid.

As already mentioned hereinbefore, the new compounds of general formula (I), the tautomers thereof and the physiologically acceptable acid-addition salts thereof display, in the case of a long period of action, superior pharmacological properties and especially a blood pressure-lowering and/or positive inotropic action and/or influence the thrombocyte function and improve the circulation.

For the preparation of pharmaceutical compositions, the compounds of general formula (I) are mixed in known manner with appropriate pharmaceutical carrier materials, aroma, flavouring and colouring materials and formed, for example, as tablets or dragees or, with the addition of appropriate adjuvants, are suspended or dissolved in water or an oil, for example olive oil.

The new compounds according to the present invention of general formula (I) and the salts thereof can be administered enterally or parenterally in liquid or solid form. As injection medium, it is preferred to use water which contains the additives usual in the case of injection solutions, such as stabilising agents, solubilising agents or buffers.

Additives of this kind include, for example, tartrate and citrate buffers, ethanol, complex formers (such as ethylenediamine-tetraacetic acid and the non-toxic salts thereof) and high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening agents.

The compounds according to the present invention are usually administered in amounts of from 10 to 500 mg. per day, referred to a body weight of 75 kg. It is preferred to administer 1 to 2 tablets with an active material content of 5 to 200 mg. two to three times a day. The tablets can also be retarded, in which case only 1 to 2 tablets with 10 to 500 mg. of active material have to be given once per day. The active material can also be administered by injection 1 to 8 times per day or by continuous infusion, amounts of 5 to 200 mg./day thereby normally sufficing.

Apart from the compounds mentioned in the Examples, preferred compounds according to the present invention include the following and the tautomers thereof:

2-(2-pyridyl)-5-(3-oxo-2,3,4,5-tetrahydro-6-pyridazinyl)-indole;

2-(5-methylthio-1.3.4-oxadiazol-2-yl)-5-(3-oxo-2,3,4,5-tetrahydro-6-pyridazinyl)-indole;

2-(1,2,5-thiadiazol-3-yl)-5-(3-oxo-2,3,4,5-tetrahydro-6-pyridazinyl)-indole;

2-(N-oxy-4-pyridyl)-5-(3-oxo-2,3,4,5-tetrahydro-6-pyridazinyl)-indole;
2-(4-nitrophenyl)-5-(3-oxo-2,3,4,5-tetrahydro-6-pyridazinyl)-indole;
2-(4-aminophenyl)-5-(3-oxo-2,3,4,5-tetrahydro-6-pyridazinyl)-indole;
2-methyl-5-(3-oxo-2,3,4,5-tetrahydro-6-pyridazinyl)-indole;
2-trifluoromethyl-5-(3-oxo-2,3,4,5-tetrahydro-6-pyridazinyl)-indole;
2-cyclopropyl-5-(3-oxo-2,3,4,5-tetrahydro-6-pyridazinyl)-indole;
2-cyano-5-(3-oxo-2,3,4,5-tetrahydro-6-pyridazinyl)-indole;
2-(5-pyrimidinyl)-5-(3-oxo-2,3,4,5-tetrahydro-6-pyridazinyl)-indole;
2-(4-imidazolyl)-5-(3-oxo-2,3,4,5-tetrahydro-6-pyridazinyl)-indole;
2-(1,2,4-triazol-3-yl)-5-(3-oxo-2,3,4,5-tetrahydro-6-pyridazinyl)-indole;
2-(2-methoxy-4-methylsulphonyloxyphenyl)-5-(3-oxo-2,3,4,5-tetrahydro-6-pyridazinyl)-indole;
2-(2-methoxy-4-propargyloxyphenyl)-5-(3-oxo-2,3,4,5-tetrahydro-6-pyridazinyl)-indole;
2-(2-methoxy-4-cyanomethyloxyphenyl)-5-(3-oxo-2,3,4,5-tetrahydro-6-pyridazinyl)-indole;
2-(2-methoxy-4-allyloxyphenyl)-5-(3-oxo-2,3,4,5-tetrahydro-6-pyridazinyl)-indole;
2-(2-methoxy-4-carboxymethyloxyphenyl)-5-(3-oxo-2,3,4,5-tetrahydro-6-pyridazinyl)-indole;
5-(3-oxo-2,3,4,5-tetrahydro-6-pyridazinyl)-indole;
2-(4-methylsulphenyl-2-methoxyphenyl)-5-(5-methyl-3-oxo-2,3,4,5-tetrahydro-6-pyridazinyl)-indole;
2-(4-methylsulphinyl-2-methoxyphenyl)-5-(5-methyl-3-oxo-2,3,4,5-tetrahydro-6-pyridazinyl)-indole;
2-(4-methylsulphonyl-2-methoxyphenyl)-5-(5-methyl-3-oxo-2,3,4,5-tetrahydro-6-pyridazinyl)-indole;
3-methyl-5(5-methyl-3-oxo-2,3,4,5-tetrahydro-6-pyridazinyl)-indole;
2,3-dimethyl-5-(5-methyl-3-oxo-2,3,4,5-tetrahydro-6-pyridazinyl)-indole;
2-methyl-3-cyano-5-(5-methyl-32,3,4,5-tetrahydro-6-pyridazinyl)-indole;
2-methyl-3-aminocarbonyl-5-(5-methyl-3-oxo-2,3,4,5-tetrahydro-6-pyridazinyl)-indole;
2-methyl-3-ethoxycarbonyl-5-(5-methyl-3-oxo-2,3,4,5-tetrahydro-6-pyridazinyl)-indole;
2-(cyclohexen-1-yl)-5-(5-methyl-3-oxo-2,3,4,5-tetrahydro-6-pyridazinyl)-indole;
2-acetyl-5-(5-methyl-3-oxo-2,3,4,5-tetrahydro-6-pyridazinyl)-indole;
2,3-diphenyl-5-(5-methyl-3-oxo-2,3,4,5-tetrahydro-6-pyridazinyl)-indole;
2-(3,4,5-trimethoxyphenyl)-5-(5-methyl-3-oxo-2,3,4,5-tetrahydro-6-pyridazinyl)-indole;
2-(2-hydroxy-5-pyrimidinyl)-5-(5-methyl-3-oxo-2,3,4,5-tetrahydro-6-pyridazinyl)-indole;
2-(4-pyrimidinyl)-5-(5-methyl-3-oxo-2,3,4,5-tetrahydro-6-pyridazinyl)-indole;
2-(4-pyridyl)-5-(5-hydroxymethyl-3-oxo-2,3,4,5-tetrahydro-6-pyridazinyl)-indole;
2-(2-methyl-4-oxazolyl)-5-(5-hydroxymethyl-3-oxo-2,3,4,5-tetrahydro-6-pyridazinyl)-indole;
2-(2-chloro-4-pyridyl)-5-(5-hydroxymethyl-3-oxo-2,3,4,5-tetrahydro-6-pyridazinyl)-indole;
2-(2-methyl-4-pyridyl)-5-(5-hydroxymethyl-3-oxo-2,3,4,5-tetrahydro-6-pyridazinyl)-indole;
2-(4-trifluoromethylsulphonyl-2-methoxyphenyl)-5-(5-hydroxymethyl-3-oxo-2,3,4,5-tetrahydro-6-pyridazinyl)-indole;
2-(4-morpholinylsulphonyl-2-methoxyphenyl)-5-(5-hydroxymethyl-3-oxo-2,3,4,5-tetrahydro-6-pyridazinyl)-indole;
2-(2-furanyl)-5-(5-hydroxymethyl-3-oxo-2,3,4,5-tetrahydro-6-pyridazinyl)-indole;
2-(2,4-dimethoxyphenyl)-5-(5hydroxymethyl-3-oxo-2,3,4,5-tetrahydro-6-pyridazinyl)-indole;
2-(4-aminosulphonyl-2-methoxyphenyl)-5-(5-hydroxymethyl-3-oxo-2,3,4,5-tetrahydro-6-pyridazinyl)-indole;
2-methyl-5-(3-cyano-6-methyl-2-oxo-1,2-dihydro-5-pyridyl)-indole;
2-phenyl-5-(3-cyano-6-methyl-2-oxo-1,2-dihydro-5-pyridyl)-indole;
2-(4-pyridazinyl)-5-(3-cyano-6methyl-2-oxo-1,2-dihydro-5-pyridyl)-indole;
2-(5-pyrimidinyl)-5-(3-cyano-6-methyl-2-oxo-1,2-dihydro-5-pyridyl)-indole;
2-(4-pyridyl)-5-(3-aminocarbonyl-6-methyl-2-oxo-1,2-dihydro-5-pyridyl)-indole; m.p. 156°–157° C.
2-(2-pyrazinyl)-5-(3-oxo-2,3,4,5-tetrahydro-1,2,4-triazin-6-yl)-indole;
2-(2-pyrrolyl)-5-(3-oxo-2,3,4,5-tetrahydro-1,2,4-triazin-6-yl)-indole;
2-(1,2,4-triazol-3-yl)-5-(3-oxo-2,3,4,5-tetrahydro-1,2,4-triazin-6-yl)-indole;
2-(2-thienyl)-5-(3-oxo-2,3,4,5-tetrahydro-1,2,4-triazin-6-yl)-indole;
2-methyl-5-(2-oxo-2,3-dihydro-6H-1,3,4-oxadiazin-5-yl)-indole;
2-(4-pyridazinyl)-5-(2-oxo-2,3-dihydro-6H-1,3,4-oxadiazin-5-yl)-indole;
2-(2-furanyl)-5-(2-oxo-2,3-dihydro-6H-1,3,4-oxadiazin-5-yl)-indole;
2-phenyl-5-(2-oxo-2,3-dihydro-6H-1,3,4-oxadiazin-5-yl)-indole;
2-(5-pyrimidinyl)-5-(6-oxo-1,4,5,6-tetrahydro-1,2,4-triazin-3-yl)-indole;
2-(2-pyrrolyl)-5-(6-oxo-1,4,5,6-tetrahydro-1,2,4-triazin-3-yl)-indole;
2-(4-pyridyl)-5-(6-oxo-1,4,5,6-tetrahydro-1,2,4-triazin-3-yl)-indole;
2-(1,2,4-triazol-3-yl)-5-(6-oxo-1,4,5,6-tetrahydro-1,2,4-triazin-3-yl)-indole;
2-methyl-5-(5-oxo-4,5-dihydro-6H-1,3,4-oxadiazin-2-yl)-indole;
2-phenyl-5-(5-oxo-4,5-dihydro-6H-1,3,4-oxadiazin-2-yl)-indole;
2-(2-pyrazinyl)-5-(5-oxo-4,5-dihydro-6H-1,3,4-oxadiazin-2-yl)-indole;
2-(2-thienyl)-5-(5-oxo-4,5-dihydro-6H-1,3,4-oxadiazin-2-yl)-indole;
2-(2-furanyl)-5-(5-oxo-4,5-dihydro-6H-1,3,4-oxadiazin-2-yl)-indole;
2-(3-pyridyl)-5-(2-oxo-1,2-dihydro-5-pyrimidinyl)-indole;
2-(4-pyridazinyl)-5-(2-oxo-1,2-dihydro-5-pyrimidinyl)-indole;
2-phenyl-5-(2-oxo-1,2-dihydro-5-pyrimidinyl)-indole;
2-trifluoromethyl-5-(2-oxo-1,2-dihydro-5-pyrimidinyl)-indole;
2-(4-pyridyl)-5-(4-methyl-2-oxo-1,2-dihydro-5-pyrimidinyl)-indole;
2-acetyl-5-(2-oxo-1,2,-dihydro-5-pyrazinyl)-indole;

2-(5-pyrimidinyl)-5-(2-oxo-1,2-dihydro-5-pyrazinyl)-indole;
2-(2-pyrazinyl)-5-(2-oxo-1,2-dihydro-5-pyrazinyl)-indole;
2-(2-pyrrolyl)-5-(2-oxo-1,2dihydro-5-pyrazinyl)-indole;
2-(4-thiazolyl)-5-(2-oxo-1,2-dihydro-5-pyrazinyl)-indole;
2-methyl-5-(4,4-dimethyl-oxo-4,5-dihydro-3-pyrazolyl)-indole;
2-phenyl-5-(4,4-dimethyl-5-oxo-4,5-dihydro-3-pyrazolyl)-indole;
2-(4-pyridazinyl)-5-(4,4-dimethyl-5-oxo-4,5-dihydro-3-pyrazolyl)-indole;
2-(2-furanyl)-5-(4,4-dimethyl-5-oxo-4,5-dihydro-3-pyrazolyl)-indole;
2-(4-thiazolyl)-5-(4,4-dimethyl-5-oxo-4,5-dihydro-3-pyrazoly)-indole;
2-(4-pyridyl)-5-(2-oxo-4-pyrrolidinyl)-indole;
2-phenyl-5-(2-oxo-4-pyrrolidinyl)-indole;
2-(4-pyridazinyl)-5-(2-oxo-4-pyrrolidinyl)-indole;
2-(2-thienyl)-5-(2-oxo-4-pyrrolidinyl)-indole;
2-(1,2,4-triazol-3-yl)-5-(2-oxo-4-pyrrolidinyl)-indole;
2-(3-pyridyl)-5-(4-methyl-5-oxo-4,5-dihydro-1,2,4-triazol-3-yl)-indole;
2-(2-pyridyl)-5-(4-methyl-5-oxo-4,5-dihydro-1,2,4-triazol-3-yl)-indole;
2-(N-oxy-4-pyridyl)-5-(4-methyl-5-oxo-4,5-dihydro-1,2,4-triazol-3-yl)-indole;
2-ethoxycarbonyl-5-(4-methyl-5-oxo-4,5-dihydro-1,2,4-triazol-3-yl)-indole;
2-trifluoromethyl-5-(4-methyl-5-oxo-4,5-dihydro-1,2,4-triazol-3-yl)-indole;
2-(4-pyridyl)-5-[4(5)-methyl-2-oxo-2,3-dihydro-5(4)-imidazolyl]-indole;
2-(4-pyridazinyl)-5-[4(5)-methyl-2-oxo-2,3-dihydro-5(4)-imidazolyl]-indole;
2-(4-pyridyl)-5-[2-oxo-2,3-dihydro-4(5)-imidazolyl]-indole;
2-methyl-5-[2-oxo-2,3-dihydro-4(5)-imidazolyl]-indole;
2-cyclopropyl-5-[2-oxo-2,3-dihydro-4(5)-imidazolyl]-indole;
2-(4-pyridyl)-5-[2-(3-oxo-2,3,4,5-tetrahydro-6-pyridazinyl)-ethyl]-indole;
2-(4-pyridazinyl)-5-[2-(3-oxo-2,3,4,5-tetrahydro-6-pyridazinyl)-ethyl]-indole;
2-phenyl-5-[2-(3-oxo-2,3,4,5-tetrahydro-6-pyridazinyl)-ethyl]-indole;
2-(4-pyridyl)-5-[2-(3-oxo-2,3,4,5-tetrahydro-6-pyridazinyl)-vinyl]-indole;
2-methyl-5-[2-(3-oxo-2,3,4,5-tetrahydro-6-pyridazinyl)-vinyl]-indole;
2-(4pyridazinyl)-5-[2-(3-oxo-2,3,4,5-tetrahydro-6-pyridazinyl)-vinyl]-indole;

The following Examples are given for the purpose of illustrating the present invention:

EXAMPLE 1

2-(4-Pyridyl)-5-(3-oxo-2,3,4,5-tetrahydro-6-pyridazinyl)-indole;

4.0 g. (21.1 mmole) 6-(4-aminophenyl)-2,3,4,5-tetrahydro-pyridazin-3-one are mixed with 70 ml. 50% sulphuric acid and cooled to 0° C. 1.53 g. (22.2 mmole) sodium nitrite, dissolved in 12 ml. water, are added dropwise thereto at 0° C. At the end of the addition, stirring is continued for 15 minutes and 0.26 g. (4.3 mmole) urea is added thereto and the reaction mixture further stirred for 15 minutes. Subsequently, a solution of 14.35 g. (63.6 mmole) stannous chloride dihydrate in 12 ml. concentrated hydrochloric acid is added dropwise thereto at 0° C. and the reaction mixture further stirred for 2 hours at 0° C. While cooling, 3.8 g. (31.4 mmole) 4-acetylpyridine are added dropwise thereto and the reaction mixture is further stirred for 2 hours at 25° C. After standing overnight, the precipitate is filtered off with suction, washed with water, again suspended in water and the pH is adjusted to 8.5 with ammonia. The solid product is filtered off with suction and dried. As crude product, there are obtained 6.76 g. 4-acetylpyridine-[4-(3-oxo-2,3,4-tetrahydro-6-pyridazinyl)-phenylhydrazone], which is reacted without further purification.

6 g. (19.5 mmole) of the hydrazone are stirred for 2 hours at 120° C. in 40 ml polyphosphoric acid under an atmosphere of nitrogen. Subsequently, the reaction mixture is poured on to ice, neutralised with a concentrated aqueous solution of ammonia and the solid product filtered off with suction. This is stirred with 1500 ml. of a warm mixture of methylene chloride/methanol (1:1 v/v), filtered and the filtrate is treated with charcoal, concentrated, filtered off with suction and purified by column chromatography (elution agent: methylene chloride/methanol 8:2 v/v). Yield 0.81 g. (14.3% of theory); m.p. 314°–316° C.

EXAMPLE 2

2-(4-Pyridyl)-3-ethyl-5-(3-oxo-2,3,4,5-tetrahydro-6-pyridazinyl)-indole;

(a) 9.45 g (49.9 mmole) 6-(4-aminophenyl)-2,3,4,5-tetrahydropyridazin-3-one are introduced into 100 ml. 2N hydrochloric acid and cooled to −2 to 0° C. 3.5 g. (50.7 mmole) sodium nitrite, dissolved in 10 ml. water, are added dropwise thereto at this temperature. Subsequently, 28 g (124 mmole) stannous chloride dihydrate, dissolved in 20.5 ml. concentrated hydrochloric acid, are added dropwise thereto and stirring is continued at 0° C. for 60 minutes. The precipitate if filtered off with suction in the cold and then washed with a little 2N hydrochloric acid and water. There are obtained 8.7 g. 6-(4-hydrazinophenyl)-2,3,4,5-tetrahydropyridazin-3-one as the hydrochloride; m.p. 243° C. (decomp.).

(b) 4 g. (16.6 mmole) of the hydrazine obtained under (a) in 50 ml. ethanol and 50 ml. water are mixed with 2.97 g. (19.9 mmole) 4-butyrylpyridine and further stirred for 3 hours at 25° C. The precipitate formed is filtered off with suction, washed with ethanol/water (1:1 v/v), again suspended in water, neutralised with an aqueous solution of ammonia and filtered off with suction. There are obtained 2.9 g. 4-butyrylpyridine-[4-(3-oxo-2,3,4,5-tetrahydro-6-pyridazinyl)-phenylhydrazone]; m.p. 243°–246° C.

(c) 2.7 g. (8 mmole) of the hydrazone obtained under (b) are heated under an atmosphere of nitrogen for 3 hours at 120° C. in 20 ml. polyphosphoric acid. The still warm solution is poured on to ice/water, worked up and filtered off with suction. The residue is again suspended in water, neutralised with an aqueous solution of ammonia, filtered off with suction and recrystallised from methanol with the addition of charcoal. There is obtained 1.65 g. (64.5% of theory) of the title compound; m.p. >300° C.

EXAMPLE 3

2-(4-Pyridyl)-3-isopropyl-5(3-oxo-2,3,4,5-tetrahydro-6-pyridazinyl)-indole.

Analogously to Example 2, from 6-(4-hydrazinophenyl)-2,3,4,5-tetrahydropyridazin-3-one and 4-(3-methylbutyrylpyridine, there is obtained a yield of 57% of theory of 4-(3-methylbutyryl)-pyridine-[4-(3-oxo-2,3,4,5-tetrahydro-6-pyridazinyl)-phenylhydrazone] (m.p. 225° C. (decomp.)) which is cyclised in polyphosphoric acid to give the title compound. Yield 41% of theory; m.p. >300° C., recrystallised from methanol.

EXAMPLE 4

2-(4-Aminocarbonylphenyl)-5-(3-oxo-2,3,4,5-tetrahydro-6-pyridazinyl)-indole

Analogously to Example 2, from 6-(4-hydrazinophenyl)-2,3,4,5-tetrahydropyridazin-3-one and p-cyanoacetophenone, there is obtained a yield of 96% of theory of p-cyanoacetophenone-[4-(3-oxo-2,3,4,5-tetrahydro-6-pyridazinyl)-phenylhydrazone] (m.p. 288°-290° C., after recrystallisation from ethanol) which is cyclised in polyphosphoric acid to give the title compound. Yield 56% of theory; m.p. >300° C.

EXAMPLE 5

2-(3-Thienyl)-5-(3-oxo-2,3,4,5-tetrahydro-6-pyridazinyl)-indole

Analogously to Example 2, from 6-(4-hydrazinophenyl)-2,3,4,5-tetrahydropyridazin-3-one and 3-acetylthiophene, there is obtained 3-acetylthiophene-[4-(3-oxo-2,3,4,5-tetrahydro-6-pyridazinyl)-phenylhydrazone] as crude product which is cyclised in polyphosphoric acid to give the title compound and purified by column chromatograpyhy (elution agent: methylene chloride/methanol saturated with ammonia 20:1 v/v). Yield 17%; m.p. 325°-333° C.

EXAMPLE 6

2-(2-Chlorophenyl)-5-(3-oxo-2,3,4,5-tetrahydro-6-pyridazinyl)-indole

Analogously to Example 2, from 6-(4-hydrazinophenyl)-2,3,4,5-tetrahydropyridazin-3-one and 2-chloroacetophenone, there is obtained 2-chloroacetophenone-[4-(3-oxo-2,3,4,5-tetrahydro-6-pyridazinyl)-phenylhydrazone] as crude product which is cyclised in polyphosphoric acid to give the title compound. Yield 39% of theory; m.p. 236°-239° C., recrystallised from ethanol/water 10:1 v/v).

EXAMPLE 7

2-(3-Trifluoromethylphenyl)-5-(3-oxo-2,3,4,5-tetrahydro-6-pyridazinyl)-indole

Analogously to Example 2, from 6-(4-hydrazinophenyl)-2,3,4,5-tetrahydropyridazin-3-one and 3-trifluoromethylacetophenone, there is obtained 3-trifluoromethylacetophenone-[4-(3-oxo-2,3,4,5-tetrahydro-pyridazinyl)-phenylhydrazone] as crude product which is cyclised in polyphosphoric acid to give the title compound, which is purified by column chromatography (elution agent: methylene chloride/methanol saturated with ammonia 20:1 v/v). Yield 30% theory; m.p. 215°-218° C., recrystallised from methanol.

EXAMPLE 8

2-(4-Pyridyl)-3-methyl-5-(3-oxo-2,3,4,5-tetrahydro-6-pyridazinyl)-indole 6-(4-Hydrazinophenyl)-2,3,4,5-tetrahydropyridazin-3-one is prepared analogously to Example 2 (a) and the suspension obtained after reduction is, without isolation of the hydrazine, mixed with 4-propionylpyridine. After 2 hours, the precipitate is filtered off with suction, again suspended in water, neutralised with an aqueous solution of ammonia and the precipitate filtered off with suction. As crude product, there is obtained 4-propionylpyridine-[4-(3-oxo-2,3,4,5-tetrahydro-6-pyridazinyl)-phenylhydrazone] (m.p. 235°-237° C.) which, without further purification, is cyclised analogously to Example 1 with polyphosphoric acid to give the title compound which is purified by column chromatography (elution agent: methylene chloride/methanol 98:2 to 90:10 v/v). Yield 24% of theory; m.p. >300° C., recrystallised from methanol.

EXAMPLE 9

2-(3-Pyridyl)-5-(3-oxo-2,3,4,5-tetrahydro-6-pyridazinyl)-indole

Analogously to Example 8, there is obtained as crude product 3-acetylpyridine-[4-(3-oxo-2,3,4,5-tetrahydro-6-pyridazinyl)-phenylhydrazone] (m.p. 236°-237° C., recrystallised from ethanol) which is cyclised in polyphosphoric acid to give the title compound. Yield 50% of theory; m.p. 298°-300° C., recrystallised from ethanol.

EXAMPLE 10

2-(4-Pyridazinyl)-5-(3-oxo-2,3,4,5-tetrahydro-6-pyridazinyl)-indole

Analogously to Example 8, there is obtained as crude product 4-acetylpyridazine-[4-(3-oxo-2,3,4,5-tetrahydro-6-pyridazinyl)-phenylhydrazone] (m.p. 258°-260° C.) which, without further purification, is cyclised in polyphosphoric acid to give the title compound which is purified by column chromatography (elution agent: methylene chloride/methanol 90:10 v/v). Yield 18% of theory; m.p. >300° C., recrystallised from methanol.

EXAMPLE 11

2-(4-Thiazolyl)-5-(3-oxo-2,3,4,5-tetrahydro-6-pyridazinyl)-indole

Analogously to Example 8, there is obtained as crude product 4-acetylthiazole-[4-(3-oxo-2,3,4,5-tetrahydro-6-pyridazinyl)-phenylhydrazone] (m.p. >300° C.) which, is without further purification, is cyclised in polyphosphoric acid to give the title compound. Yield 39% theory; m.p. 307°-309° C., recrystallised from methanol.

EXAMPLE 12

2-(2-Pyrazinyl)-5-(3-oxo-2,3,4,5-tetrahydro-6-pyridazinyl)-indole ×0.5 mole ethanol Analogously to Example 8, there is obtained as crude product 2-acetylpyrazine-[4-(3-oxo-2,3,4,5-tetrahydro-6-pyridazinyl)-phenylhydrazone] (m.p. 197°-202° C.) which, without further purification, is cyclised in polyphosphoric acid to give the title compound. Yield 8.4% of theory; m.p. 284°-286° C., recrystallised from ethanol.

EXAMPLE 13

2-Phenyl-5-(3-oxo-2,3,4,5-tetrahydro-6-pyridazinyl)-indole

Analogously to Example 8, there is obtained as crude product acetophenone-[(3-oxo-2,3,4,5-tetrahydro-6-pyridazinyl)-phenylhydrazone] (m.p. 176°–178° C.) which, without further purification, is cyclised in polyphosphoric acid to give the title compound and purified b column chromatography (elution agent: methylene chloride/methanol 9:1 v/v). Yield 45% of theory; m.p. 270°–275° C.

EXAMPLE 14

2-(4-Methoxyphenyl)-5-(3-oxo-2,3,4,5-tetrahydro-6-pyridazinyl)-indole

Analogously to Example 8, there is obtained as crude product p-methoxyacetophenone-[4-(3-oxo-2,3,4,5-tetrahydro-6-pyridazinyl)-phenylhydrazone] (m.p. 204°–207° C.) which, without further purification, is cyclised in polyphosphoric acid to give the title compound and purified by column chromatography (elution agent: methylene chlorine/methanol 9:1). Yield 8% of theory; m.p. 262°–264° C.

EXAMPLE 15

2-(4-Methylphenyl)-5-(3-oxo-2,3,4,5-tetrahydro-6-pyridazinyl)-indole

Analogously to Example 8, there is obtained as crude product 4-methylacetophenone-[4-(3-oxo-2,3,4,5-tetrahydro-6-pyridazinyl)-phenylhydrazone] (m.p. 102°–104° C.) which, without further purification, is cyclised in polyphosphoric acid to give the title compound. Yield 5.1% of theory; m.p. 266°–268° C., recrystallised from ethanol.

EXAMPLE 16

2-(4-Methylthiophenyl)-5-(3-oxo-2,3,4,5-tetrahydro-6-pyridazinyl)-indole

Analogously to Example 8, there is obtained as crude product 4-methylthioacetophenone-[4-(3-oxo-2,3,4,5-tetrahydro-6-pyridazinyl)-phenylhydrazone] (m.p. 126°–128° C.) which, without further purification, is cyclised in polyphosphoric acid to give the title compound. Yield 8.9% of theory; m.p. 256°–258° C., recrystallised from dioxan.

EXAMPLE 17

2-(2-Hydroxyphenyl)-5-(3-oxo-2,3,4,5-tetrahydro-6-pyridazinyl)-indole×0.5 mole, ethanol Analogously to Example 8, there is obtained as crude product 2-hydroxyacetophenone-[4-(3-oxo-2,3,4,5-tetrahydro-6-pyridazinyl)-phenylhydrazone] (m.p. 88°–96° C.) which, without further purification, is cyclised in polyphosphoric acid to give the title compound. The crude product is dissolved in ethanol, treated with charcoal, filtered, the filtrate evaporated and the residue triturated with diethyl ether. Yield 12.4% of theory; m.p. 238°–240° C.

EXAMPLE 18

2-[4-(Imidazole-1-yl)-phenyl]-5-(3-oxo-2,3,4,5-tetrahydro-6-pyridazinyl)-indole

Analogously to Example 8, there is obtained as crude product 4-(imidazol-1-yl)-acetophenone-[4-(3-oxo-2,3,4,5-tetrahydro-6-pyridazinyl)-phenylhydrazone] (m.p. >300° C.) which, without further purification, is cyclised in polyphosphoric acid to give the title compound which is then purified by column chromatography (elution agent: methylene chloride/methanol 95:5 v/v). Yield 25% of theory; m.p. 295°–298° C.

EXAMPLE 19

2-(4-Pyridyl)-5-(5-methyl-3-oxo-2,3,4,5-tetrahydro-6-pyridazinyl)-indole

Starting from 6-(4-aminophenyl)-5-methyl-2,3,4,5-tetrahydropyridazin-3-one, analogously to Example 2 (a), there is obtained 6-(4-hydrazinophenyl)-5-methyl-2,3,4,5-tetrahydropyridazin-3-one which, after reduction, is reacted, without isolation, with 4-acetylpyridine. After 3 hours, the precipitate if filtered off with suction, again suspended in water, neutralised with an aqueous solution of ammonia and the precipitated filtered off with suction and recrystallised from ethanol. There is obtained a yield of 65% of theory of 4-acetylpyridine-[4-(3-oxo-5-methyl-2,3,4,5-tetrahydro-6-pyridazinyl)-phenylhydrazone] (m.p. 246°–248° C., recrystallised from ethanol). The hydrazone thus obtained is cyclised with polyphosphoric acid analogously to Example 1 to give the title compound. Yield 78% of theory; m.p. 301°–303° C., recrystallised from methanol.

EXAMPLE 20

2-(2,5-Thiadiazol-3-yl)-5-(5-methyl-3-oxo-2,3,4,5-tetrahydro-6-pyridazinyl)-indole Analogously to Example 19, there is obtained as crude product 3-acetyl-1,2,5-thiadiazole-[4-(3-oxo-5-methyl-2,3,4,5-tetrahydro-6-pyridazinyl)-phenylhydrazone] (m.p. 241°–245 ° C.) which, without further purification, is crystallised in polyphosphoric acid to give the title compound. Yield 48% of theory; m.p. >300° C., recrystallised from ethanol.

EXAMPLE 21

2-(4-Pyridyl)-3-methyl-5-(5-methyl-3-oxo-2,3,4,5-tetrahydro-6-pyridazinyl)-indole Analogously to Example 19, there is obtained 4-propionylpyridine-4-(4-(3-oxo-5-methyl-2,3,4,5-tetrahydro-6-pyridazinyl)-phenylhydrazone] in a yield of 58% of theory (m.p. 233°–235° C.) which is cyclised in polyphosphoric acid to give the title compound. Yield 53% of theory; m.p. 294°–297° C.

EXAMPLE 22

Ethyl-5-(3-oxo-2,3,4,5-tetrahydro-6-pyridazinyl)-indole-2-carboxylate 3.02 g (10 mmole) pyruvic acid ethyl ester ]4-(3-oxo-2,3,4,5-tetrahydro-6pyridazinyl)-phenylhydrazone] is cyclised analogously to Example 1 in polyphosphoric acid to give the title compound. Yield 0.71 g. (25% of theory); m.p. 235°–237° C., recrystallised from fiethyl ether.

The starting material can be prepared as follows:

A solution of 1.6 g. sodium nitrite in 5 ml. water is added dropwise, at a temperature below +5° C., to a mixture of 4.0 g. (21 mmole) 6-(4-aminophenyl)-2,3,4,5-tetrahydro-pyridazin-3-one, 5.1 ml. concentrated hydrochloric acid and 25 g ice. The reaction mixture is further stirred for 60 minutes at 0° C., and filtered.

To a mixture of 3.0 g. (21 mmole) ethyl 2-methylacetoacetate and 25 g. ice are added dropwise and simultaneously the above filtrate, as well as a cooled solution of 5.1 g. potassium hydroxide in 13 ml. water. The reaction mixture is stirred for 30 minutes at 0° C., 20 g. ice are added thereto and also 3.9 ml. concentrated hydrochloric acid and filtered.

The sticky residue is taken up in dichloromethane and a little methanol, dried over anhydrous sodium sulphate, evaporated and triturated with diethyl ether. There are obtained 4.7 g. (7.4% of theory) pyruvic acid ethyl ester [4-(3-oxo-2,3,4,5-tetrahydro-6-pyridazinyl)-phenylhydrazone]; m.p. 189°–191° C.

EXAMPLE 23

5-(3-Oxo-2,3,4,5-tetrahydro-6-pyridazinyl)-indole-2-carboxylic acid 3 g. (10.5 mmole) of the ester obtained in Example 22 are heated under reflux for 2 hours with 1.6 g. potassium hydroxide and 25 ml. 70% ethanol. The reaction mixture is evaporated in a vacuum, the residue is taken up in water, washed with diethyl ether and the aqueous phase acidified. 1.8 g. (67% of theory) of the title compound precipitate out; m.p. 185°–187° C.

EXAMPLE 24

2-(4-Pyridyl)-5-(2-oxo-1,2-dihydro-5-pyrazinyl)-indole ×1.5 mole water

Starting from 5-(4-aminophenyl)-1,2-dihydropyrazin-2-one, there is obtained, analogously to Example 2 a), 5-(4-hydrazinophenyl)-1,2-dihydropyrazin-2-one which, after reduction, is mixed, without isolation, with 4-acetylpyridine. After 3 hours, the residue is filtered off with suction, again suspended in water, neutralised with an aqueous solution of ammonia and the precipitate filtered off with suction. There is obtained, as crude product, 4-acetylpyridine-[4-(2-oxo-1,2-dihydro-5-pyrazinyl)-phenylhydrazone] (m.p. 175°–179° C.) which, witout further purification, is cyclised with polyphosphoric acid analogously to Example 1 to give the title compound. Yield 30% of theory; m.p. >300° C. recrystallised from methanol.

Example 25

2-(4-Pyridyl)-5-(2-oxo-2,3-dihydro-6H-1,3,4-oxadiazin-5-yl)-indole (a) Analogously to Example 2 (a), starting from 5-(4-aminophenyl)-2,3-dihydro-6H-1,3,4-oxadiazin-2-one, there is obtained, in a yield of 64% of theory, 5-(4-hydrazinophenyl)-2,3-dihydro-6H-1,3,4-oxadiazin-2-one as hydrochloride; m.p. 210°–220° C.

(b) 9.1 g. (33 mmole) of the hydrazine obtained according to (a) in 100 ml. methanol are mixed with 3.5 ml. (33 mmole) 4-acetylpyridine and stirred for 1 hour at 25° C. The precipitated crystals are filtered off with suction and washed with a little methanol. There are obtained 10 g. (98% of theory) 4-acetylpyridine[4-(2-oxo-2,3-dihydro-6H-1,3,4-oxadiazin-5-yl)-phenylhydrazone] as hydrochloride; m.p. 290°–295° C.

(c) Analogously to Example 2 (c), 10 g. (30 mmole) of the hydrazone obtained according to (b) are cyclised in polyphosphoric acid to give the title compound. Yield 6.9 g. (73% of theory); m.p. 322°–325° C., recrystallised from ethanol.

EXAMPLE 26

2-(4-Pyridyl)-5-(3-oxo-2,3,4,5-tetrahydro-1,2,4-triazin-6-yl)-indole (a) Analogously to Example 2 (a), starting from 6-(4-aminophenyl)-2,3,4,5-tetrahydro-1,2,4-triazin-3-one, there is obtained, in a yield of 65% of theory, 6-(4-hydrazinophenyl)-2,3,4,5-tetrahydro-1,2,4-triazin-3-one as hydrochloride; m.p. 249°–259° C.

(b) Analogously to Example 25 (b), from the hydrazine according to (a) and 4-acetylpyridine, there is obtained, in a yield of 63% of theory, 4-acetylpyridine-8 4-(3-oxo-2,3,4,5-tetrahydro-1,2,4-triazin-6-yl)-phenylhydrazone] as hydrochloride; m.p. >300° C.

(c) Analogously to Example 2 (c), 5.5 g. (18 mmole) of the hydrazone according to (b) are cyclised in polyphosphoric acid to give the title compound and purified by column chromatography (elution agent: methylene chloride/ethanol/glacial acetic acid 10:1:0.2 v/v/v). The evaporated fractions are again suspended in water, neutralised with an aqueous solution of ammonia and filtered off with suction. Yield 1.8 g. (35% of theory); m.p. 313°–316° C.

EXAMPLE 27

2-(4-Pyridyl)-5-(5-oxo-4,5-dihydro-6H-1,3,4-oxadiazin-2-yl)-indole ×1 mole dimethylformamide (a) 3.2 g. 1-(4-nitrobenzoyl)-2-chloroacetylhydrazine are dissolved in 62.5 ml. anhydrous dimethylformamide, 0.88 g. of a 50% suspension of sodium hydride in oil is added thereto, the reaction mixture is stirred for 15 minutes at 120° C., then evaporated to dryness at an oil pump vacuum at 60° C., the residue is triturated with a little water and the crystals obtained are filtered off with suction, there being obtained 2 g. 2-(4-nitrophenyl)-4,5-dihydro-6H-1,3,4-oxadiaxin-5-one; m.p. 224°–229° C., recrystallised from methanol.

(b) 1.5 g. of the nitro compound obtained according to (a) is hydrogenated in 150 ml. methanol and 2.3 ml. glacial acetic acid at 25° C. in the presence of 0.75 g. 10% palladium on charcoal. After filtering off the catalyst, the filtrate is evaporated and the residue triturated with diethyl ether. There is obtained, as crude product, 1 g. 2-(4-aminophenyl)-4,5-dihydro-6H-1,3,4-oxadiazin-5-one m.p. 238°–245° C.

(c) Analogously to Example 2 (a), from the so obtained amine there is prepared 2-(4-hydrazinophenyl)-4,5-dihydro-6H-1,3,4-oxadiazin-5-one and the suspension obtained after reduction thereof is mixed, without isolation of the hydrozine, with the 4-acetylpyridine. The reaction mixture is further stirred for 3 hours with suction and washed with water. There is thus obtained, as a crude product, 4-acetylpyridine-[4-(5-oxo-4,5-dihydro-6H-1,3,4-oxadiazin-2-yl)-phenylhydrazone]; m.p. 195° C.

(d) Analogously to Example 2 (c) 0.7 g. of the hydrazone obtained according to (c) is cyclised in polyphosphoric acid to give the title compound and this is then dissolved in a little dimethylformamide and purified by column chromatography (elution agent: ethyl acetate/methanol 9:1 v/v). Yield 90 mg.; m.p. 273°–277° C.

EXAMPLE 28

2-(4-Pyridyl)-4-(4-methyl-5-oxo-4,5-dihydro-1,2,4-triazol-3-yl)-indole (a) 1.81 g. 4-Nitrobenzoylhydrazide is dissolved in 80 ml. anhydrous hot dioxan, this solution is mixed at 40° C. with a solution of 0.7 g. methyl isocyanante in 5 ml. dioxan, then stirred for 30 minutres, at 25° C. and the resultant crystallisate is filtered off with suction, there thus being obtained 2.2 g. 1-(4-nitrobenzoyl)-4-methyl-semicarbazide; m.p. 254°–256° C.

(b) 2 g. of this semicarbazide are dissolved in 20 ml. 1N aqueous sodium hydroxide solution, heated to 130° C. for 7.5 hours, cooled and neutralised with 2N hydrochloric acid. The crystallisate is filtered off with suction and washed with water and ethanol to give 1.3 g. crude 3-(4-nitrophenyl)-4-methyl-1,2,4-triazol-5-one; m.p. 290°–298° C.

(c) 2.2 g. of the nitro compound obtained according to (b) are suspended in 160 ml. methanol and hydrogenated in the presence of 0.6 g. 10% palladium on charcoal. After separating off the catalyst, the filtrate is evaporated in a vacuum. There is thus obtained 1.6 g. crude 3-(4-aminophenyl)-4-methyl-1,2,4-triazol-5-one; m.p. 228°–230° C.

(d) Analogously to Example 2 (a), from the so obtained amine is prepared 3-(4-hydrazinophenyl)-4-methyl-1,2,4-triazol-5-one and the suspension obtained after reduction is mixed without isolation of the hydrazine, with 4-acetylpyridine. The reaction mixture is further stirred for 4 hours at 25° C. and the precipitate is filtered off with suction and washed with water and diethyl ether. There are thus obtained 2 g. crude 4-acetylpyridine-[4-(5-oxo-4,5-dihydro-4-methyl-1,2,4-triazol-3yl)-phenylhydrazone] as hydrochloride.

(e) Analogously to Example 2 (c), 1 g. of the hydrazone obtained according to (d) is cyclised in polyphosphoric acid to give the title compound. The crude product is repeatedly boiled out with ethanol, separated from insoluble material while still hot and treated with charcoal at an elevated temperature. The filtrate is evaporated and the crystallisate thereby obtained is filtered off with suction and washed with ethanol and diethyl ether. Yield 0.13 g.; m.p. >300° C.

EXAMPLE 29

2-(4-Pyridyl)-5-(4,4-dimethyl-5-oxo-4,5-dihydro-3-pyrazoyl)-indole (a) A solution of 23.7 g. (0.1 mole) ethyl 2-(4-nitrobenzoyl)-acetate in 100 ml. tetrahydrofuran is added dropwise to a suspension of 9.6 g. (0.2 mole) 50% sodium hydride in 30 ml. anhydrous dimethylformamide, 12.5 ml. methyl iodide are added thereto and the reaction mixture is stirred for 20 hours at ambient temperature. Thereafter, it is poured into 1 liter of water and extracted with diethyl ether. The extracts are dried adn evaporated, there being obtained 25.4 g. ethyl 2-(4-nitrobenzoyl)-isobutyrate in the form of an oily crude product.

(b) A mixture of 17.0 g. (64 mole) of the above crude product, 9.0 ml. hydrazine hydrate and 150 ml. ethanol is heated under reflux for 18 hours, subsequently evaporated in a vacuum and chromatographed on a silica gel, elution being carried out with dichloromethane/methanol (19:1 v/v). There are obtained 8.1 g. (54% of theory) 3,4-dihydro-4,4-dimethyl-5-(4-nitrobenzoyl)-3-oxopyrazole as an oil.

(c) 8.0 g. (34 mmole) of the above nitro compound are hydrogenated in 200 ml. methanol in the presence of 1 g. Raney nickel at 1 bar hydrogen pressure. After 2 hours, the reaction mixture is filtered, the filtrate is evaporated and the residue triturated with diethyl ether. There are obtained 5.7 g. (83% theory) 5-(4-aminobenzoyl)-3,4-dihydro-4,4-dimethyl-3-oxopyrazole; m.p. 198°–200° C.

(d) 3.0 g. (15 mmole) of the above amino compound are mixed with 60 ml. 2N hydrochloric acid and cooled to 0° C. A solution of 1.2 g. sodium nitrite in 10 ml. water is added dropwise thereto, the reaction mixture is stirred for 5 minutes at 0° C., a solution of 9.8 g. stannous chloride in 30 ml. 2N hydrochloric acid is added dropwise thereto, the reaction mixture is stirred for 30 minutes at ambient temperature, filtered and the filtrate mixed with 2.5 ml. 4-acetylpyridine. The reaction mixture is stirred for 5 hours at ambient temperature, left to stand overnight, filtered and the precipitate dried in a vacuum. There are obtained 5.7 g. (98% of theory) 4-acetylpyridine-[4-(4,4-dimethyl-4-oxo-4,5-dihydro-3-pyrazolyl)-phenylhydrazone] as dihydrochloride; m.p. 271°–274° C.

(e) 2.0 g. (6 mmole) of the above hydrazone are stirred with 50 g. polyphosphoric acid for 10 minutes at 120° C. The reaction mixture is poured on to ice, rendered alkaline with ammonia, filtered, the precipitate is taken up with dichloromethane/methanol (9:1 v/v), decolorised with animal charcoal and evaporated. After trituration with ligroin, there is obtained the title compound. Yield 0.34 g. (16% of theory); m.p. 300° C.

EXAMPLE 30

2-Methyl-3-phenyl-5-(3-oxo-2,3,4,5-tetrahydro-6-pyridazinyl)-indole 4.8 g. (20 mmole) 6-(4-hydrazinophenyl)-2,3,4,5-tetrahydropyridazin-3-one hydrochloride (according to Example 2 (a)) are suspended in 75 ml. 2N hydrochloric acid and 75 ml. ethanol, mixed with 2.8 g. (21 mmole) phenylacetone, stirred for 3 hours at 25° C., filtered off with the suction and the title compound obtained is recrystallised from methanol. Yield 4.85 g. (80% of theory); m.p. 297°–299° C.

EXAMPLE 31

2-(4-Pyridazinyl)-5-(5-methyl-3-oxo-2,3,4,5-tetrahydro-6-pyridazinyl)-indole

Analogously to Example 19, there is obtained, in a yield of 70% of theory, 4-acetylpyridazine-[4-(3-oxo-5-methyl-2,3,4,5-tetrahydro-6-pyridazinyl)-phenylhydrazone] (m.p. 265° C. (decomp.)) which is cyclised in polyphosphoric acid to give the title compound. Yield 29%; m.p. 293°–295° C., recrystallised from methanol.

Pharmaceutical Activity

The following experiment demonstrates the pharmaceutical activity of compound (I) of the invention:

Male Sprague-Dawley rats weighing between 350 and 450 g were narcotized by intraperitoneal injection of a barbiturate and fitted with instrumentation for the examinations as follows:

A pressure measuring catheter (Millar Mikrotip TM /diameter 0.5 mm) was inserted through the arteria carotis dextra into the left ventricle. The pressure inside the left ventricle was continually registered through this catheter. The signal from this mikrotip was electronically differentiated and $(dp/dt)_{60}$—the slope of the pressure-time curve at a pressure of 60 mm Hg—was taken as a measure for the inotropy.

A polypropylene catheter was bound in a vena jugularis for the intravenous injection of the test substances.

A further polypropylene catheter was inserted through an arteria femoralis into the abdominal aorta for the direct measurement of the arterial blood pressure.

The ECG was traced with subcutaneous insertion electrodes.

During the preparation of the animal and during the entire test period the rats were fixed on a electrically heated and thermostated operating table.

The test substances were always introduced by intravenous injection, with an injection volume, per injection, of 1 ml/kg body weight. In intervals of 10 min. each, dose increasing from 0.01 to 30 mg of the test substances were intravenously injected. In this way dose effect curves for the measured parameters for the investigated substances were obtained.

From the measured data, using a regression calculation, equipotent doses for the positively inotropic effect $(dp/dt)_{60}$ were calculated. In addition, as criteria for the effectiveness of the substances, the maximum effect obtained maximal increase of $(dp/dt)_{60}$ and its corresponding dose were determined. Table (I) below shows the equipotent doses ($DE_{1.5}$=the dose in mg/kg that leads to an increase of $(dp/dt)_{60}$ of 1.5 mHg/sec) and the maximal effectiveness ($W_{max}$=the maximal increase of $(dp/dt)_{60}$.

TABLE I

| Compound | $DE_{1.5}$ mHg/sec [mg/kg i.v.] | $W_{max}$ [mHg/sec] | [mg/kg i.v.] |
|---|---|---|---|
| 1 | 0,04 | >3,1 | 1,0 |
| 8 | 0,08 | 2,9 | 0,3 |
| 10 | 0,01 | 2,5 | 0,1 |
| 11 | 0,26 | 2,5 | 1,0 |
| 24 | 0,15 | 3,4 | 3,0 |
| Ref. 1 | 1,17 | 3,5 | 10,0 |
| Ref. 2 | 3,0 | 0,6 | 3,0 |

The corresponding dose is shown in brackets.
Ref. 1: 3-Amino-6-methyl-5-phenyl-2-(1H)—pyridinone-methane-sulfonate (from British Patent Application GB 2,070,606).
Ref. 2: 3,4-Dihydro-6-[4-(3,4-dimethoxybenzoyl)-1-piperazinyl]-2(1H)—quinolinone (from U.S. Pat. Application U.S. 4,415,572).

It will be understood that the specification and examples are illustrative but not limitative of the present invention and that other embodiments within the spirit and scope of the invention will suggest themselves to those skilled in the art.

What is claimed is:

1. A compound of the formula:

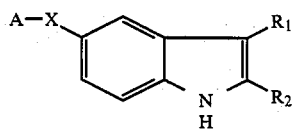

wherein $R_1$ is hydrogen, methyl, ethyl, isopropyl or phenyl;
$R_2$ is a heterocyclic five-membered ring containing 1 to 4 heteroatoms or a heterocyclic six-membered ring containing 1 to 4 heteroatoms selected from the group consisting of pyrrole, furan, thiophene, pyrazole, imidazole, thiazole, oxazole, triazole, tetrazole, thiadiazole, oxadiazole, pyridine, N-oxypyridine, pyrazine, N,N-dioxypyrazine, pyrimidine, N,N-dioxypyrimidine, pyridazine, oxazine, thiazine, triazine and tetrazine, said five- and six-membered rings optionally being substituted by one or more $C_1-C_6$ alkyl, $C_1-C_6$ alkoxy, $C_1-C_6$ alkylthio, hydroxyl, nitro, amino, halogen or cyano groups; or $R_2$ is a phenyl ring of the formula:

$$\begin{array}{c} R_5 \\ R_4 \\ \\ R_3 \end{array} \quad (II)$$

wherein $R_3$, $R_4$ and $R_5$ are the same or different and each represents: hydrogen; $C_1-C_5$ alkyl-sulphonyloxy; trifluoromethanesulphonyloxy; $C_1-C_5$ alkyl-sulphonyamino; trifluoromethanesulphonylamino; N-$C_1-C_5$-alkyl-$C_1-C_5$-alkyl-sulphonylamino; N-$C_1-C_5$-alkyl-trifluoromethanesulphonylamino; $C_1-C_5$-alkyl-sulphenylmethyl; $C_1-C_5$-alkyl-sulphinylmethyl; $C_1-C_5$-alkylsulphonylmethyl; a carbonyl group substituted by hydroxyl, $C_1-C_5$ alkoxy, amino, $C_1-C_5$ alkylamino oor di-$C_1-C_5$-alkyl-amino; a sulphonyl group substituted by amino, $C_1-C_5$ alkylamino or di-$C_1-C_4$-alkyl-amino; a morpholino-, pyrrolidino-, piperidino-, or hexamethyleneimino-sulphonyl radical; $C_1-C_5$ alkylcarbonylamino; amino-carbonylamino; $C_1-C_5$ alkyl-aminocarbonylamino; $C_1-C_5$ alkylthio; $C_1-C_5$ alkylsulphinyl; $C_1-C_5$ alkylsulphonyl; nitro; halogen; amino; hydroxyl; $C_1-C_5$-alkyl; $C_1-C_5$ alkoxy; $C_2-C_5$ alkenyloxy; $C_2-C_5$ alkynyloxy; cyano-$C_1-C_5$-alkoxy; carboxy-$C_1-C_5$-alkoxy; $C_1-C_5$-alkoxy-carbonyl-$C_1-C_5$-alkoxy; di-$C_1-C_5$-alkylamino; 1-imidazolyl; trifluoromethyl; or cyano;

A is a heterocyclic radical selected from the group consisting of 3-oxo-2,3-dihydro-6-pyridazinyl, 5-alkyl-3-oxo-2,3-dihydro-6-pyridazinyl, 3-oxo-2,3,4,5-tetrahydro-6-pyridazinyl, 5-alkyl-3-oxo-2,3,4,5-tetrahydro-6-pyridazinyl, 5-hydroxyalkyl-3-oxo-2,3,4,5-tetrahydro-6-pyridazinyl, 3-cyano-6-alkyl-2-oxo-1,2-dihydro-5-pyridinyl, 3-aminocarbonyl-6-alkyl-2-oxo-1,2-dihydro-5-pyridinyl, 6-alkyl-2-oxo-1,2-dihydro-5-pyridinyl, 3-amino-6alkyl-2-oxo-1,2-dihydro-5-pyridinyl, 3-hydroxy-6-alkyl-2-oxo-1,2-dihydro-5-pyridinyl, 3-oxo-2H-3,4-dihydro-1,4-thiazin-6-yl, 6-oxo-1,6-dihydro-1,2,4-triazin-3-yl, 6-oxo-1,4,5,6-tetrahydro-1,2,4-triazin-3-yl, 5-oxo-4,5-dihydro-6H-1,3,4-oxadiazin-2-yl, 5-oxo-4,5-dihydro-6H-1,3,4-thiadiazin-2-yl, 3-oxo-2,3-dihydroo-1,2,4-triazin-6-yl, 3-oxo-2,3,4,5-tetrahydro-1,2,4-triazin-6-yl, 2-oxo-2,3-dihydro-6H-1,3,4-oxadiazin-5-yl, 2-oxo-2,3-dihydro-6H-1,3,4-thiadiazin-5-yl, 5-alkyl-3-oxo-2,3,4,5-tetrahydro-1,2,4-triazin-6-yl, 2-oxo-1,2-dihydro-5-pyrimidinyl, 4-alkyl-2-oxo-1,2-dihydro-5-pyrimidinyl, 2-oxo-1,2-dihydro-5-pyrazinyl, 3-alkyl-2-oxo-1,2-dihydro-5-pyrazinyl, 6-alkyl-2-oxo-1,2-dihydro-5-pyrazinyl, 4,4-dialkyl-5-oxo-4,5-dihydro-3-pyrazolyl, 2-oxo-4-pyrrolidinyl, 3-alkyl-2-oxo-4-pyrrolidinyl, 5-oxo-4,5-dihydro-1,2,4-triazol-3-yl, 4-alkyl-5-oxo-4,5-dihydro-1,2,4-triazol-3-yl, 2-oxo-2,3-dihydro-4(5)-imidazolyl and 5(4)-alkyl-2-oxo-2,3-dihydro-4(5)-imidazolyl;

X is a valency bond or a $C_1-C_4$ alkylene or vinylene group,
a tautomer thereof or
a physiologically acceptable salt thereof with an inorganic or organic acid.

2. A compound of claim 1 wherein $R_2$ is pyrrole, furan, thiophene, pyrazole, imidazole, thiazole, oxazole, thiazole, tetrazole, thiadiazole, oxadiazole, pyridine, N-oxy-pyridine, pyrazine, N,N-dioxypyrazine, pyramidine, N,N-dioxpyrimidine, pyridazine, oxazine, thiazine, triazine, tetrazine, or the methyl, ethyl, methoxy, ethoxy, methylthio, ethylthio or chlorine substituted derivative thereof; of $R_2$ is said phenyl ring of formula (II) wherein $R_3$ is hydrogen, methanesulphonyloxy, trifluoromethanesulphonyloxy, methansulphonylamino, trifluoromethanesulphonylamino, N-methyl-methanesulphonylamino, N-methyl-trifluoromethanesulphonylamino, methylsulphenylmethyl, methylsulphinylmethyl, methylsulphonylmethyl, aminocarbonyl, aminosulphonyl, methylaminosulphonyl, dimethylaminosulphonyl, acetylamino, methylthio, methylsulphonyl, hydroxyl, methyl, methoxy, propargyloxy, cyanomethoxy, methoxycarbonylmethoxy, cyano, chloro, nitro, amino, dimethylamino, trifluoromethyl or 1-imidazolyl; $R_4$ is hydrogen, methyl, methoxy, dimethylamino or chlorine; and $R_5$ is hydrogen atom or methoxy;

A is 3-oxo-2,3,4,5-tetrahydro-6-pyridazinyl, 5-methyl-3-oxo-2,3,4,5-tetrahydro-6-pyridazinyl, 5-hydroxymethyl-3-oxo-2,3,4,5-tetrahydro-6-tetrahydro-6-pyridazinyl, 3-cyano-6-methyl-2-oxo-1,2-dihydro-5-pyridinyl, 3-aminocarbonyl-6-methyl-2-oxo-1,2-dihydro-5-pyridinyl, 3-oxo-2,3,4,5-tetrahydro-1,2,4-triazin-6-yl, 2-oxo-4,5-dihydro-6H-1,3,4-oxadiazin-5-yl, 6-oxo-1,4,5,6-tetrahydro-1,2,4-triazin-3-yl, 5-oxo-4,5-dihydro-6H-1,3,4-oxadiazin-2-yl, 2-oxo-1,2-dihydro-5-pyrimidinyl, 2-oxo-1,2-dihydro-5-pyrazinyl, 4,4-dimethyl-5-oxo-4,5-dihydro-3-pyrazolyl, 2-oxo-4-pyrrolidinyl, 4-methyl-5-oxo-4,5-dihydro-1,2,4-triazol-3-yl or 5(4)-methyl-2-oxo-2,3-dihydro-4(5)-imidazolyl and X is a valency bond, vinylene or ethylene, or a tautomer thereof or a physiologically acceptable salt thereof with an inorganic or organic acid.

3. A compound of claim 2 wherein $R_2$ is thiophene, thiazole, thiadiazole, pyridine, pyrazine or pyridazine, or a phenyl which is optionally substituted by an aminocarbonyl, chlorine, trifluoromethyl, methyl, methoxy, methylthio, hydroxy or 1-imidazolyl radical;

A is 3-oxo-2,3,4,5-tetrahydro-6-pyridazinyl, 5-methyl-3-oxo-2,3,4,5-tetrahydro-6-pyridazinyl, 2-oxo-1,2-dihydro-5-pyrazinyl, 2-oxo-2,3-dihydro-6H-1,3,4-oxadiazin-5-yl, 3-oxo-2,3,4,5-tetrahydro-1,2,4-triazin-6-yl, 5-oxo-4,5-dihydro-6H-1,3,4-oxadiazin-2-yl, 4-methyl-5-oxo-4,5-dihydro-1,2,4-triazol-3-yl or 4,4-dimethyl-5-oxo-4,5-dihydro-3-pyrazolyl, and X is a valency bond or vinylene, a tautomer thereof or a physiologically acceptable salt thereof with an inorganic or organic acid.

4. A compound of claim 2 wherein $R_2$ is pyrrole, furan, thiophene, pyrazole, imidazole, thiazole, oxazole, triazole, tetrazole, thiadiazole, oxadiazole, pyridine N-oxypyridine, pyrazine, N,N-dioxypyrazine, pyrimidine, N,N-dioxypyrimidine, pyridazine, oxazine, thiazine, triazine, tetrazine, or a methyl, ethyl, methoxy, ethoxy, methylthio, ethylthio or chlorine substituted derivative thereof.

5. A compound of claim 2 wherein $R_2$ is said phenyl ring of formula (II).

6. The compound of claim 4 designated 2-(4-pyridyl)-5-(3-oxo-2,3,4,5-tetrahydro-6-pyridazinyl)-indole.

7. The compound of claim 4 designated 2-(4-pyridyl)-3-methyl-5-(3-oxo-2,3,4,5-tetrahydro-6-pyridazinyl)-indole.

8. The compound of claim 4 designated 2-(4-pyridazinyl)-5-(3-oxo-2,3,4,5-tetrahydro-6-pyridazinyl)-indole.

9. The compound of claim 4 designated 2-(4-thiazolyl)-5-(3-oxo-2,3,4,5-tetrahydro-6-pyridazinyl)-indole.

10. The compound of claim 4 designated 2-(4-pyridyl)-5-(2-oxo-1,2-dihydro-5-pyrazinyl)-indole.

11. A pharmaceutical composition containing an effective amount of at least one compound oof claim 1 for the prophylaxis or treatment of heart and circulatory diseases in a pharmaceutically acceptable carrier.

12. A pharmaceutical composition containing an effective amount of at least one composition of claim 4 for the prophylaxis or treatment of heart and circulatory diseases in a pharmaceutically acceptable carrier wherein said compound is 2-(4-pyridyl)-5-(3-oxo-2,3,4,5-tetrahydro-6-pyridazinyl)-indole, 2-(4-pyridyl)-3-methyl-5-(3-oxo-2,3,4,5-tetrahydro-6-pyridazinyl)-indole, 2-(4-pyridazinyl)-5-(3-oxo-2,3,4,5-tetrahydro-6-pyridazinyl)-indole, 2-(4-thiazolyl)-5-(3-oxo-2,3,4,5-tetrahydro-6-pyridazinyl)-indole, 2-(4-pyridyl)-5-(2-oxo-1,2-dihydro-5-pyrazinyl)-indole or 2-(4-pyridyl)-5-(5-methyl-3-oxo-2,3,4,5-tetrahydro-6-pyridazinyl)-indole.

13. A method for the treatment of heart and circulatory diseases comprising administering an effective amount of the composition of claim 11.

14. A method for treatment of heart and circulatory diseases comprising administering an effective amount of a compound of claim 1.

15. A method for prophylaxis of heart and circulation diseases comprising administering an effective amount of a compound of claim 2.

16. The method of claim 14, wherein 10 to 500 mg of compound, per 75 Kg body weight, are administered per day.

17. The method of claim 15, wherein 10 to 500 mg of compound, per 75 Kg body weight, are administered per day.

18. The compound of claim 4 designated 2-(4-pyridyl)-5-(5-methyl-3-oxo-2,3,4,5-tetrahydro-6-pyridazinyl)-indole.

* * * * *

UNITED STATES PATENT AND TRADEMARK OFFICE
CERTIFICATE OF CORRECTION

PATENT NO. : 4,851,406

DATED : July 25, 1989

INVENTOR(S) : Alfred Mertens, et al.

It is certified that error appears in the above-identified patent and that said Letters Patent is hereby corrected as shown below:

Col. 2, line 61, "ehtyl" should read ethyl".

Col. 3, line 30, "eloxy" should read "enyloxy".

Col. 6, line 10, "Hetrocyclic" should read "Heterocyclic".

Col. 8, line 31, "can ve" should read "can be".

Col. 13, line 43, "323,4,5" should read ""3-oxo-2,3,4,5".

Col. 17, line 38, "chromatograpyhy" should read "chromatography".

Col. 18, line 55, "39% theory" should read "39% of theory".

Col. 19, line 10, "b " should read "by".

Col. 20, line 65, "60" should read "30".

Col. 21, line  8, "7.4%" should read "74%".

Col. 22, line  7, "8 4-(3-oxo-" should read "[4-(3-oxo".

Col. 22, line 45, "hydrozine" should read "hydrazine".

UNITED STATES PATENT AND TRADEMARK OFFICE
CERTIFICATE OF CORRECTION

PATENT NO. : 4,851,406

DATED : July 25, 1989

INVENTOR(S) : Alfred Mertens, et al.

It is certified that error appears in the above-identified patent and that said Letters Patent is hereby corrected as shown below:

Col. 22, line 47, "3 hours with suction" should read "3 hours at 25°C. and the precipitate obtained is filtered off with suction".

Col. 23, line 46, "adn" should read "and".

Col. 26, line 13, Claim 1, "sulphonyamino" should read "sulphonylamino".

Col. 26, line 20, Claim 1, "oor" should read "or".

Col. 26, line 41, Claim 1, "3-amino-6alkyl-2-oxo-" should read "3-amino-2-oxo-".

Col. 26, line 42, Claim 1, "3-hydroxy" should read "3-amino".

Col. 26, line 49, Claim 1, "dihydroo" should read "dihydro".

Col. 27, line 4, Claim 2, "pyramidine" should read "pyrimidine".

Col. 27, line 26, Claim 2, "6-tetrahydro-6-pyridazinyl" should read "6-pyridazinyl,".

Col. 28, line 23, Claim 11, "oof" should read "of".

UNITED STATES PATENT AND TRADEMARK OFFICE
CERTIFICATE OF CORRECTION

PATENT NO. : 4,851,406

DATED : July 25, 1989

INVENTOR(S) : Alfred Mertens, et al.

It is certified that error appears in the above-identified patent and that said Letters Patent is hereby corrected as shown below:

Col. 28, line 23, Claim 11, "oof" should read "of".

Signed and Sealed this

Eighth Day of January, 1991

*Attest:*

HARRY F. MANBECK, JR.

*Attesting Officer*  *Commissioner of Patents and Trademarks*